United States Patent
Sridhar et al.

(10) Patent No.: US 10,912,480 B2
(45) Date of Patent: Feb. 9, 2021

(54) SENSOR SYSTEM AND PROCESS FOR MEASURING ELECTRIC ACTIVITY OF THE BRAIN, INCLUDING ELECTRIC FIELD ENCEPHALOGRAPHY

(71) Applicant: Northeastern University, Boston, MA (US)

(72) Inventors: Srinivas Sridhar, Newton, MA (US); Yury Petrov, Wakefield, MA (US); Ozgur Yavuzcetin, Fort Atkinson, WI (US); Kaushik Chowdhury, Boston, MA (US)

(73) Assignee: Northeastern University, Boston, MA (US)

( * ) Notice: Subject to any disclaimer, the term of this patent is extended or adjusted under 35 U.S.C. 154(b) by 798 days.

(21) Appl. No.: 14/896,511

(22) PCT Filed: Jun. 20, 2014

(86) PCT No.: PCT/US2014/043425
§ 371 (c)(1),
(2) Date: Dec. 7, 2015

(87) PCT Pub. No.: WO2014/205356
PCT Pub. Date: Dec. 24, 2014

(65) Prior Publication Data
US 2016/0120432 A1 May 5, 2016

Related U.S. Application Data

(60) Provisional application No. 61/837,692, filed on Jun. 21, 2013.

(51) Int. Cl.
*A61B 5/0478* (2006.01)
*A61B 5/00* (2006.01)
(Continued)

(52) U.S. Cl.
CPC ........ *A61B 5/0478* (2013.01); *A61B 5/04004* (2013.01); *A61B 5/4082* (2013.01);
(Continued)

(58) Field of Classification Search
CPC .............................. A61B 5/04; A61B 5/04004
See application file for complete search history.

(56) References Cited

U.S. PATENT DOCUMENTS 3,565,060 A 2/1971 Sipple
4,559,950 A 12/1985 Vaughan et al.
(Continued)

FOREIGN PATENT DOCUMENTS

EP 1615550 B1 3/2007
JP 20110136158 A1 7/2011
(Continued)

OTHER PUBLICATIONS

L. H. Kahane, et al., "Regression Basics Chapter 2: The Least-Squares Estimation Method", Second Edition, Sage Publications, Inc. 2008, Retrieved from the internet: <URL: http://www.sagepub.com/upm-data/17668_Chapter2.pdf>, 22 pgs.
(Continued)

*Primary Examiner* — Puya Agahi
(74) *Attorney, Agent, or Firm* — Verrill Dana, LLP

(57) ABSTRACT

A sensor system and process for measuring electromagnetic activity of a brain are provided. The system and process employ a sensor assembly having a plurality of electrodes arranged in a closely spaced arrangement and a processor to determine a weighted average of the signals indicative of an electric field generated by electromagnetic activity of the brain. The system provides a medical body area network of a subject including one or more of the sensor assemblies and one or more additional sensors, which may be within a smartphone or other wearable device.

11 Claims, 18 Drawing Sheets

(51) Int. Cl.
*A61B 5/04* (2006.01)
*A61B 5/11* (2006.01)

(52) U.S. Cl.
CPC .......... *A61B 5/4088* (2013.01); *A61B 5/4094* (2013.01); *A61B 5/6814* (2013.01); *A61B 5/6898* (2013.01); *A61B 5/0006* (2013.01); *A61B 5/0024* (2013.01); *A61B 5/1117* (2013.01); *A61B 5/6831* (2013.01); *A61B 5/7203* (2013.01); *A61B 5/7278* (2013.01); *A61B 5/746* (2013.01); *A61B 2503/40* (2013.01); *A61B 2562/0219* (2013.01); *A61B 2562/0223* (2013.01); *A61B 2562/046* (2013.01)

(56) References Cited

U.S. PATENT DOCUMENTS

| | | | |
|---|---|---|---|
| 4,649,482 | A | 3/1987 | Raviv et al. |
| 4,791,593 | A | 12/1988 | Hennion |
| 4,800,888 | A | 1/1989 | Itil et al. |
| 5,148,149 | A | 9/1992 | Campbell et al. |
| 5,613,495 | A | 3/1997 | Mills et al. |
| 5,704,365 | A | 1/1998 | Albrecht et al. |
| 5,724,984 | A | 3/1998 | Arnold et al. |
| 5,797,853 | A | 8/1998 | Musha et al. |
| 6,161,030 | A | 12/2000 | Levendowski et al. |
| 6,195,576 | B1 | 2/2001 | John |
| 6,449,461 | B1 | 9/2002 | Otten |
| 6,807,438 | B1 | 10/2004 | Brun Del Re et al. |
| 6,871,084 | B1 | 3/2005 | Kingsley et al. |
| 6,873,872 | B2 | 3/2005 | Gluckman et al. |
| 7,141,987 | B2 * | 11/2006 | Hibbs .................... A61B 5/04 324/658 |
| 8,032,209 | B2 | 10/2011 | He et al. |
| 8,190,248 | B2 | 5/2012 | Besio et al. |
| 8,437,843 | B1 | 5/2013 | Kayyali et al. |
| 2003/0021518 | A1 | 1/2003 | Smirnov |
| 2003/0093129 | A1 | 5/2003 | Nicolelis et al. |
| 2003/0204148 | A1 | 10/2003 | Lange et al. |
| 2004/0097802 | A1 * | 5/2004 | Cohen ................. A61B 5/04004 600/411 |
| 2004/0158119 | A1 | 8/2004 | Osorio et al. |
| 2005/0073322 | A1 * | 4/2005 | Hibbs .................... A61B 5/04 324/658 |
| 2005/0215916 | A1 | 9/2005 | Fadem et al. |
| 2006/0173510 | A1 | 8/2006 | Besio |
| 2006/0251303 | A1 | 11/2006 | He |
| 2007/0048707 | A1 * | 3/2007 | Caamano ............. A61B 5/0002 434/236 |
| 2007/0073184 | A1 | 3/2007 | Lu et al. |
| 2007/0106143 | A1 | 5/2007 | Flaherty |
| 2007/0250134 | A1 | 10/2007 | Miesel et al. |
| 2009/0177073 | A1 | 7/2009 | Sonnenborg |
| 2010/0100153 | A1 | 4/2010 | Carlson et al. |
| 2010/0113961 | A1 | 5/2010 | Ohlander et al. |
| 2010/0145176 | A1 | 6/2010 | Himes |
| 2011/0190625 | A1 | 8/2011 | Harlev et al. |
| 2011/0282231 | A1 | 11/2011 | Pradeep et al. |
| 2011/0295096 | A1 | 12/2011 | Bibian et al. |
| 2012/0116725 | A1 * | 5/2012 | Klinkenbusch ........ G01R 29/10 702/189 |
| 2012/0136273 | A1 | 5/2012 | Michelson, Jr. |
| 2012/0302858 | A1 | 11/2012 | Kidmose et al. |
| 2012/0316459 | A1 | 12/2012 | Abreu |
| 2013/0009783 | A1 | 1/2013 | Tran |
| 2013/0035578 | A1 | 2/2013 | Chiu et al. |
| 2013/0079860 | A1 | 3/2013 | Besio |
| 2013/0138010 | A1 | 5/2013 | Nierenberg et al. |
| 2013/0310676 | A1 * | 11/2013 | Jung .................... A61B 5/6803 600/383 |
| 2016/0081577 | A1 * | 3/2016 | Sridhar ................. A61B 5/4064 600/383 |

FOREIGN PATENT DOCUMENTS

| | | |
|---|---|---|
| WO | 20110088227 A1 | 7/2011 |
| WO | 20120068493 A1 | 5/2012 |
| WO | 2014/025353 A1 | 2/2014 |

OTHER PUBLICATIONS

Y. Petrov, "Harmony: EEG/MEG Linear Inverse Source Reconstruction in the Anatomical Basis of Spherical Harmonics", PLOS ONE, Oct. 2012, vol. 7, Issue 10, 15 pgs.

R. Doost-Mohammady, et al., "Enhancing Wireless Medical Telemetry through Dynamic Spectrum Access", Proc. of IEEE ICC, Jun. 2012, pp. 1603-1608.

R. Doost-Mohammady, et al., "Transforming Healthcare and Medical Telemetry through Cognitive Radio Networks", IEEE Wireless Communications Magazine, Aug. 2012, vol. 19, No. 4, pp. 67-73.

C. E. Vasios, et al., "EEG/(f)MRI measurements at 7 Tesla using a New EEG cap (InkCAp)", NeuroImage, Dec. 2006, vol. 33, Issue 4, pp. 1082-1092.

O. Vaisanen, et al., "Improving the SNR of EEG generated by deep sources with weighted multi-electrode leads", Journal of Physiology-Paris, Nov. 2009, vol. 103, Issue 6, pp. 306-314.

P. L. Nunez, et al., "EEG coherency II: experimental comparisons of multiple measures", Clinical Neurophysiology, (1999), vol. 110, pp. 469-486.

A. B. Usakli, "Improvement of EEG Signal Acquisition: An Electrical Aspect for State of the Art of Front End", Computational Intelligence and Neuroscience, Jan. 2010, vol. 2010, 7 pgs.

Y. Petrov, et al., "Electric Field Encephalography as a Tool for Functional Brain Research: A Modeling Study", PLOS ONE, Jul. 2013, vol. 8, Issue 7, 9 pgs.

Y. Petrov, et al., "Ultra-dense EEG sampling results in two-fold increase of functional brain information", Neuroimage, (2014), vol. 90, pp. 140-145.

Baillet, S. et al., "Combined MEG and EEG source imaging by minimization of mutual information", IEEE Trans. Biomed. Eng., vol. 46, No. 5, pp. 522-534 (May 1999).

Gibson, R.S., "Slab-Coupled Optical Fiber Sensors for Electrical Field Sensing Applications", All Theses and Dissertations, Paper 1942, 164 pages (Dec. 2009).

Gutierrez-Martinez, C. et al., "Modeling and experimental electro-optic response of dielectric lithium niobate , waveguides used as electric field sensors", Measurement Science and Technology, vol. 22, 035207 (7 pgs.) (Feb. 15, 2011).

Haueisen, J. et al., "The influence of Brain Tissue Anistrophy on Human EEG and MEG", NeuroImage, vol. 15, pp. 159-166 (2002).

Komssi, S. et al., "EEG minimum-norm estimation compared with MEG dipole fitting in the localization of somatosensory sources at S1", Clinical Neurophysiology, vol. 115, pp. 534-542 (2004).

Liu, A. K. et al., "Monte Carlo simulation studies of EEG and MEG localization accuracy", Human Brain Mapping, vol. 16, pp. 47-62 (2002).

Malmivuo, J., "Comparison of the properties of EEG and MEG in detecting the electric activity of the brain", Brain Topogr., vol. 25, pp. 1-19 (Jan. 2012).

Prance, R. J. et al., "Remote detection of human electrophysiological signals using electric potential sensors", Applied Physics Letters, vol. 93. pp. 033906-1-33906-3 (2008).

Ramon, C. et al., "Influence of head models on neuromagnetic fields and inverse source localizations", BioMedical Engineering Online, vol. 5, pp. 1-13 (2006).

Runde, D. et al., "Integrated optical electric field sensor based on a Bragg grating in lithium niobate", Applied Physics B., Laser and Optics, vol. 86, pp. 91-95 (2007).

Wolters, C. H. et al., "Influence of tissue conductivity anisotrophy on EEG/MEG field and return current computation in a realistic head model: A simulation and visualization study using high-resolution finite modeling", Neuroimage, vol. 30, pp. 813-826 (2006).

(56) References Cited

OTHER PUBLICATIONS

Kamrunnahar, M. et al., "Toward a Model-Based Predictive Controller Design in Brain-Computer Interfaces", Annals of Biomedical Engineering, May 2011, vol. 39, No. 5, pp. 1482-1492.

* cited by examiner

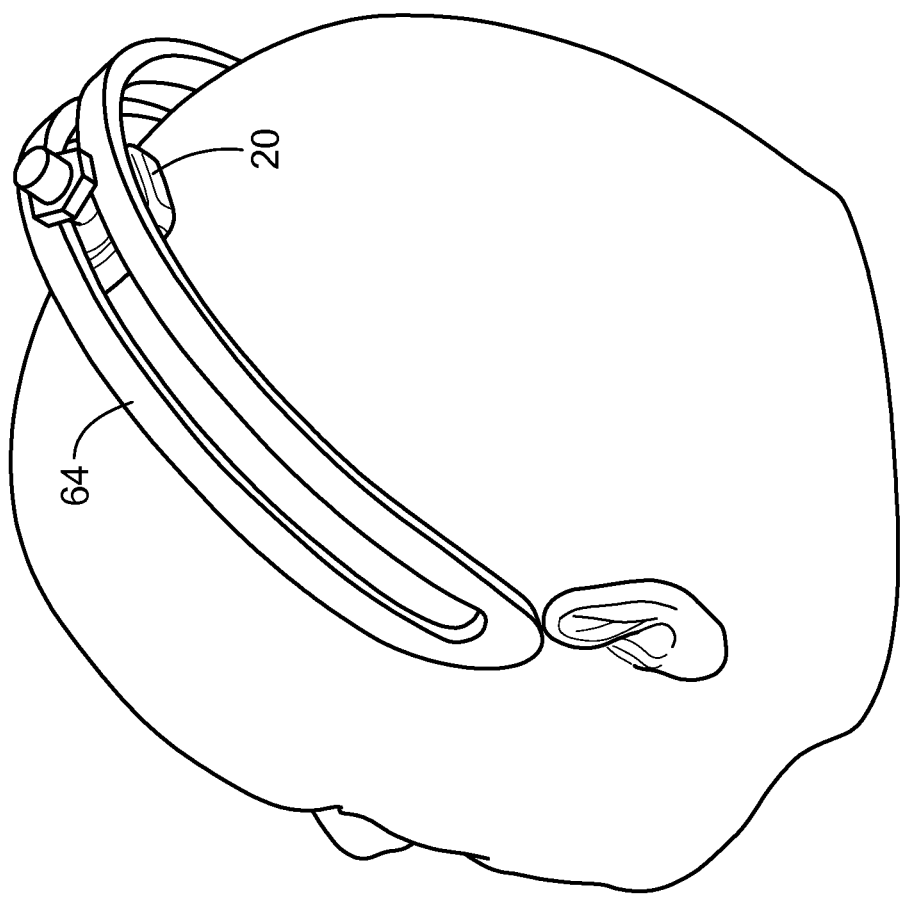
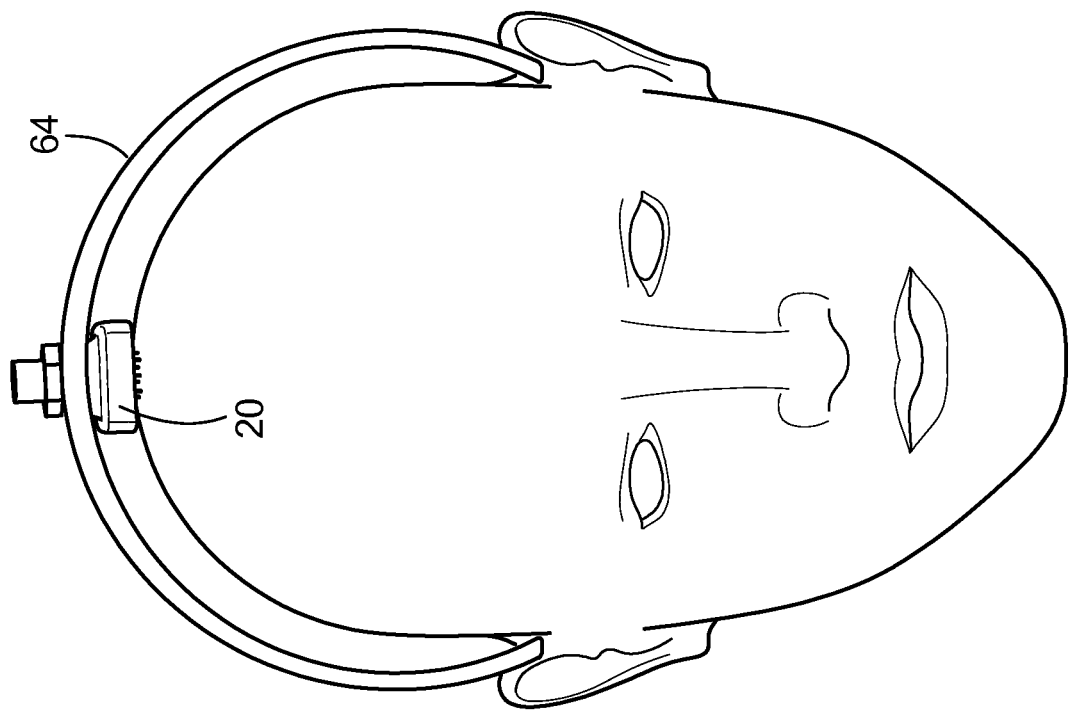
FIG. 5B
FIG. 5A

SENSOR SYSTEM AND PROCESS FOR MEASURING ELECTRIC ACTIVITY OF THE BRAIN, INCLUDING ELECTRIC FIELD ENCEPHALOGRAPHY

CROSS-REFERENCE TO RELATED APPLICATIONS

This application claims the benefit under 35 U.S.C. § 119(e) of U.S. Provisional Patent Application No. 61/837,692, filed Jun. 21, 2013, entitled Novel Sensors for Electric Field Encephalography, the disclosure of which is incorporated by reference herein.

STATEMENT REGARDING FEDERALLY SPONSORED RESERCH OR DEVELOPMENT

This invention was made with government support under Grant Number 1264216 awarded by the National Science Foundation. The government has certain rights in the invention.

BACKGROUND

The gold standard for locating and measuring electrical activity in the human brain is the use of intracranial electrodes, as in electrocorticography (eCOG). This technique is expensive and risky. It is used only in rare clinical cases and is limited to configurations that have been approved by the FDA.

Thus, there is a need for non-invasive and affordable tools that can approach eCOG is terms of spatial and temporal resolution. The human brain emits electric and magnetic signals that can be detected outside of the head, provided instruments with sufficient sensitivity are available. Non-invasive brain signal monitoring is an integral tool in a variety of research and clinical settings. Current methods include electroencephalography (EEG), magnetoencephalography (MEG), functional magnetic resonance imaging (fMRI), and functional near infrared spectroscopy (fNIRS).

While fMRI provides high spatial resolution over the whole head volume, it is limited in temporal resolution (1 to 10 seconds), convenience, and portability. Also, it does not provide a direct measure of neuronal activity.

EEG samples electric potential across the scalp and MEG samples the magnetic field several centimeters from the scalp's surface. With these techniques, a large number of sensors, such as 64 to 256, are applied to a subject's scalp.

Miniaturization of EEG sensors is severely impeded by the need to compensate for degradation in signal quality. Electrode separation in EEG ranges from 10 cm to 3 cm, which is still insufficient for high resolution measurements. EEG utilizes a global reference, and accordingly, local measurements are contaminated by global brain activity, such that local measurements at high resolution are not feasible. The global reference electrode and the grounding electrode require wiring across the scalp. EEG also suffers from time and difficulty in setting up the electrodes on a subject's skull and subsequently removing the electrodes. Some popular high-density EEG systems use liquid electrolytes, which decreases the setup time to several minutes. Additionally, liquid electrolytes can lead to conductive bridges, which significantly increase cross-talk between nearby electrodes and further limit EEG's spatial resolution. Dry electrodes are severely noise limited. Also, present electrodes do not work well with very thick and curly hair types.

Typical scalp electric potentials produced by brain activity are extremely weak, on the order of several microvolts, which are comparable with the internal noise of amplifiers used for EEG (0.1 to 0.5 microvolts). This, in combination with external sources of noise, makes raw EEG signals very noisy. With the exception of strong brain rhythms, such as alpha and beta, EEG signals have to be averaged over dozens of repeated trials in order to average out the noise and to obtain a usable signal-to-noise ratio (SNR). For many applications, however, such as brain-computer interfaces, sleep research, epilepsy research, and many other practical cases of EEG-based biometrics, EEG averaging is impossible, because of the unique nature of each event.

Magnetoencephalography (MEG) overcomes some of the problems of EEG, notably that of reference and grounding. However, MEG faces other problems with noise reduction, necessitating expensive infrastructure that precludes any mobility of the subject.

SUMMARY OF THE INVENTION

The present invention relates to a sensor system and process for measuring electromagnetic activity of the brain, including electric field activity. Unlike electric potential, measured by electroencephalography (EEG), electric fields associated with brain activity have not generally been studied because the signals are weak. The electric field vector is given by the negative gradient of the electric potential (measured by EEG) and can provide additional information. The present system can measure local electric fields, referred to as electric field encephalography (EFEG), as well as electric potentials and higher order derivatives of the potential, such as the Laplacian, on a human scalp. By averaging over a large number of sensors in a small measuring area, an acceptable signal-to-noise ratio (NSR) can be achieved.

In one aspect, the system includes a sensor assembly for measuring electric field and potential activity of a brain, comprising a plurality of electrodes supported by a support plate. The electrodes are arranged in a closely spaced arrangement, and one of the plurality of electrodes comprises a reference electrode. A plurality of amplifiers, each associated with one of the plurality of electrodes, are arranged on the second side of the support plate. A microcontroller is also supported by the support plate in communication with the amplifiers. The microcontroller includes a processor operative to determine a weighted average of the signals indicative of an electric field generated by electromagnetic activity of the brain.

In other aspects, the microcontroller can determine an electric potential indicative of electromagnetic activity of the brain and can determine a higher order spatial derivative of the electric potential. The sensor assembly of the system can include a transceiver for sending and receiving signals between the microcontroller and an external device and can include a wireless data transmission port.

The sensor assembly can include a housing attached to the support plate, with the plurality of amplifiers and the microcontroller disposed within the housing. In further aspects, the plurality of electrodes can be arranged with an inter-spacing of 1 cm or less, or with an interspacing of 4 mm or less, or with an interspacing of 3 mm or less, and can be arranged in a variety of patterns, including a hexagonal pattern, a circular pattern, a triangular pattern, a square pattern, or in no regular pattern.

In another aspect, a process for measuring electromagnetic activity of a brain comprises placing a plurality of electrodes in an arrangement on a scalp, each of the electrodes in electrical communication with an associated amplifier; defining a reference electrode among the plurality of electrodes; measuring a potential difference between active electrodes of the plurality of electrodes and the reference electrode; and determining a weighted average of the potential differences, the weighted average indicative of electrical activity of the brain.

In other aspects, the process includes determining an electric potential indicative of electromagnetic activity of the brain and determining a higher order derivative of the electric potential. The process can include generating an image of brain activity of the subject.

In still further aspects, a method for improving a signal-to-noise ratio of measurements of electromagnetic activity of a brain is provided, comprising placing a plurality of electrodes in an arrangement on a scalp, each of the electrodes in electrical communication with an associated amplifier; defining a reference electrode among the plurality of electrodes; measuring a potential difference between each of the plurality of electrodes and the reference electrode; and determining a weighted average of the potential differences, the weighted average indicative of electrical activity of the brain. The plurality of electrodes can be supported on a support plate and a plurality of amplifiers can be supported on the support plate in close proximity to the electrodes.

In further aspects, a method for concurrently measuring electric potentials and electric fields of a brain is provided, comprising placing a plurality of electrodes in an arrangement on a scalp, each of the electrodes in electrical communication with an associated amplifier; defining a first reference electrode among the plurality of electrodes; defining a further reference electrode spaced remotely from the plurality of electrodes; switching between measuring a potential difference between active electrodes of the plurality of electrodes and the first reference electrode and measuring a potential difference between each of the plurality of electrodes and the further electrode; and determining a weighted average of the potential differences and a weighted average of the potentials, the weighted averages indicative of electrical activity of the brain.

In still further aspects, a method for measuring brain activity of a subject is provided, comprising placing a plurality of electrodes in an arrangement on a scalp, each of the electrodes in electrical communication with an associated amplifier; defining a reference electrode among the plurality of electrodes; measuring a potential difference between active electrodes of the plurality of electrodes and the reference electrode; determining a weighted average of the potential differences, the weighted average indicative of electrical activity of the brain. The method can include generating an image of brain activity of the subject. The subject may suffer from a neurological condition; or from Alzheimer's disease, Parkinson's disease, amyotrophic lateral sclerosis, stroke, traumatic brain injury, autism, depression, or epilepsy. In a still further aspect, the method includes treating the subject for the neurological condition. In a still further aspect, the method includes comparing the brain activity of the subject to the brain activity of a normal subject, and detecting a neurological condition of the subject based on the comparison of the brain activity of the subject to the brain activity of the normal subject.

In a further aspect, a system for providing a medical body area network of a subject includes one or more sensor assemblies for measuring electromagnetic activity of a brain of the subject, each sensor assembly including a support plate, a plurality of electrodes protruding from the support plate, the electrodes arranged in a closely spaced arrangement, one of the plurality of electrodes comprising a reference electrode, a plurality of amplifiers supported by the support plate, each amplifier of the plurality of amplifiers associated with one of the plurality of electrodes to receive signals from the associated ones of the electrodes indicative of electric field activity of a brain, and a microcontroller in communication with the amplifiers to receive signals from the amplifiers, the microcontroller operative to determine a weighted average of the signals indicative of an electric field generated by electromagnetic activity of the brain. One or more additional sensors for monitoring physiological parameters of the subject are provided, the other sensors comprising at least one of a GPS device, an accelerometer, a gyroscope, a magnetometer, a microphone, and a camera. A processor is operative to receive data from the one or more sensor assemblies and the one or more additional sensors and to synchronize the data.

The processor and the one or more of the additional sensors can reside within a smartphone. The system can include a database of sensor readings indicative of one of a variety of activities, such as include watching TV, sitting, eating, walking, or exercising. The system can transmit the synchronized data to a host processor, a cloud computing facility, or an external computer.

DESCRIPTION OF THE DRAWINGS

The invention will be more fully understood form the following detailed description taken in conjunction with the accompanying drawings in which:

FIG. 5A is a schematic front view of a headband supporting a sensor assembly;

FIG. 5B is a schematic isometric view of the headband and sensor assembly of FIG. 5A;

DETAILED DESCRIPTION OF THE INVENTION

The present sensor system and process are capable of electric field encephalography (EFEG) as well as EEG. The sensor system employs a sensor assembly utilizing a plurality of sensors closely spaced in an array. For each sensor, the system can determine the electric potential (EEG), the electric field components (EFEG), and higher order derivatives of the potential, such as its surface Laplacian. From the measured electric field data, an estimate of the location of the electric field sources can be made and an image of brain activity can be generated.

The system employs a number, N, of sensors, each associated with an active independent amplifier. By averaging over multiple noisy sensors, rather than over multiple noisy trials, an acceptable signal-to-noise ratio (SNR) can be achieved. Assuming independent noise for each sensor's amplifier pair (the active amplifier and a reference amplifier), the associated SNR increase is given by the square root of the convergence ratio.

Figures 3, 4:
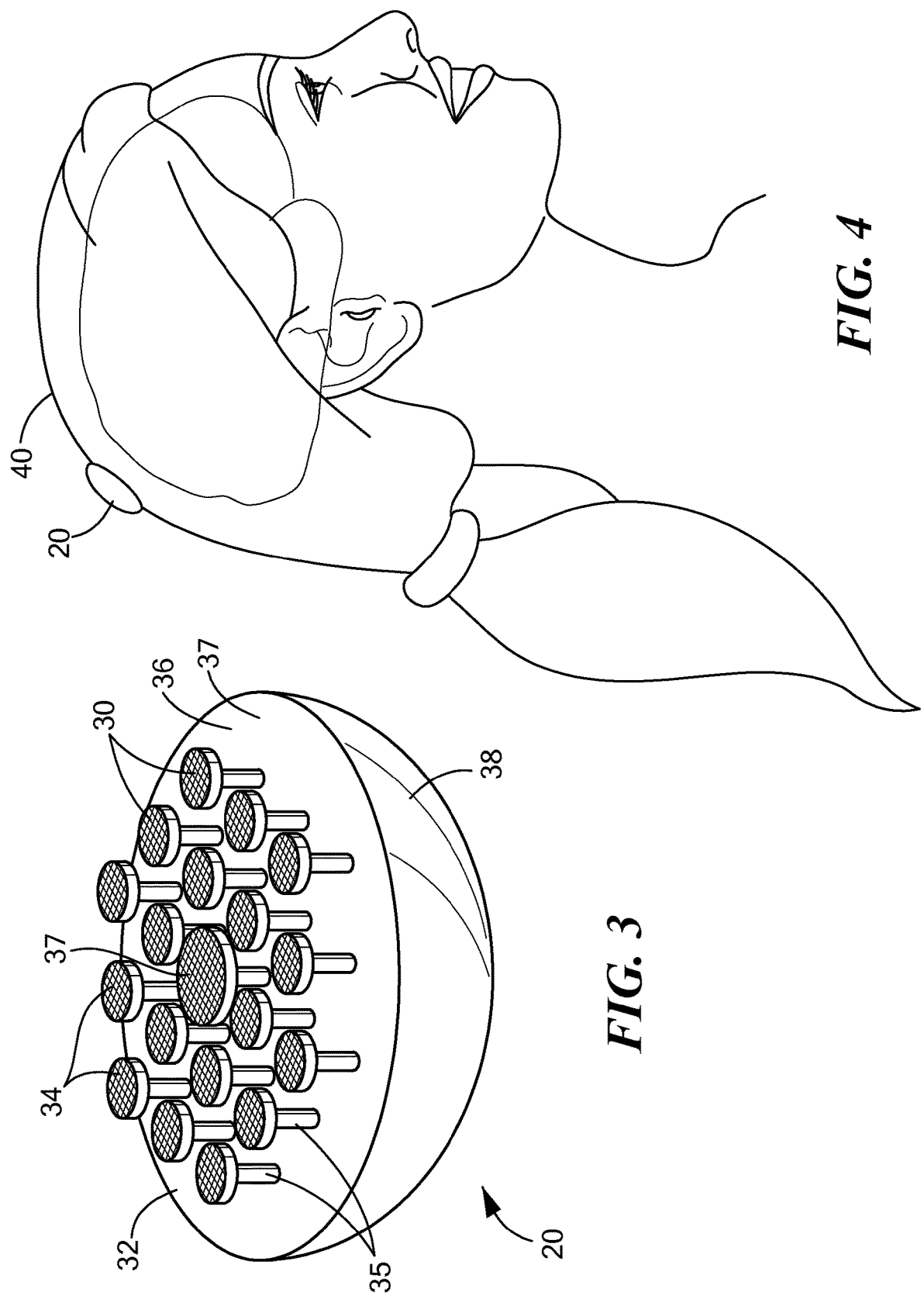
FIG. 3 is a bottom perspective view of a further embodiment of a sensor assembly.
FIG. 4 is a side view of a sensor assembly in use applied to a subject's scalp.

Referring to FIGS. 1-4, the sensor system includes a sensor assembly 20 supporting a plurality of individual sensors 30 arranged in an array 32. Each sensor is an electrode 34 having a suitable configuration for making good electrical contact with the scalp. In some embodiments, each electrode is in the form of an electrically conductive pin 35. The end or tip of each pin can be, for example, convexly rounded (FIG. 2), cup-shaped or concave, or waffle-shaped (FIG. 3). The configuration of the tip or end can depend on the hair type (for example, curly, straight, fine, thick) and amount (for example, heavy, thin, balding) of the subject. The electrodes can be pressed into contact with the scalp if desired, for example, with a spring mechanism. Suitable electrode materials include silver, gold, copper, and alloys thereof. In one embodiment, the electrodes are formed with a silver core and a Ag/Cl coating on the surface to prevent or minimize DC polarization at the scalp-electrode interface. Other electrode or electric field sensor configurations can be used if desired. Other sensor configurations can include electro-optical sensors such as photonic crystals made of lithium niobate.

In some embodiments, the sensor assembly 20 includes a support plate 36 or other structure for mounting or supporting the electrodes 34. The pins 35 of the electrodes extend through the support plate to protrude from a first side 37. Electronic components 42 that interface with the electrodes (described further below) are mounted on or supported by the other, second side of the support plate 36. (See FIG. 1.) Connections between the electrodes and the electronic components are made on the second side of the support plate. The sensor assembly also includes a housing or cover 38 to enclose the electronic components. The housing is sized to attach to an area of the scalp of a subject 40 with the protruding electrodes in electrical contact with the scalp. See FIG. 4. The housing or cover can be grasped by a user when placing the sensor assembly on a subject's scalp. The sensor assembly is sufficiently small such that several sensor assemblies can be attached to the subject's scalp if desired.

The electrodes 34 supported by a sensor assembly 20 can be arranged in any suitable array 32, and any suitable number, N, of electrodes can be provided. The electrodes can be more closely spaced than the electrodes used in traditional EEG. Electrode density can be, for example, 0.3 $cm^{-2}$, 1.0 $cm^{-2}$, 4.0 $cm^{-2}$, or greater. Lesser electrode densities can also be used, if desired, depending on the application. For example, in one embodiment, 19 electrodes are arranged in a hexagonal array (FIGS. 2, 3) with an interspacing of 3 to 4 mm. The array is 2 cm in diameter at its widest dimension. The combined area of the 19 electrodes, when applied to a scalp surface, is a few square centimeters. In another example, 16 electrodes are arranged in a square 4×4 array. The electrode interspacing is 1 cm. It will be appreciated that the electrodes can be arranged in other patterns, such as circular, triangular, or the like, or in no regular pattern, and the term "array" can encompass all such patterns or no pattern.

The sensor assembly 20 including the housing 38 can be sufficiently miniaturized that it can be attached to a scalp relatively unobtrusively. The sensor assembly can be formed with a lower profile than the profile of currently used EEG sensors. The sensor assembly can be attached to the scalp in any suitable manner. For example, in some embodiments, the sensor assembly can be attached with tape or an adhesive suitable for use on skin and hair. In other embodiments, the sensor assembly can be held in place with a device such as a headband or a headset. The sensor assembly can be integrally formed with the headband or headset. The headband or headset can be adjustable to fit a variety of head sizes and shapes. The headband or headset can be configured to support more than one sensor assembly, such as 2, 3, 4, or more sensor assemblies. See, for example, FIGS. 5A and 5B, which illustrate a headset supporting a sensor assembly 20 supported by a band 64 on a subject's head. In most cases, setup time can be 5 minutes or less. In most cases, reliable electrical contact with the scalp can be made without the use of liquid or gel electrolytes, which can create electrical bridges and severely reduce the spatial resolution of dry electrode EEG.

Figure 6:
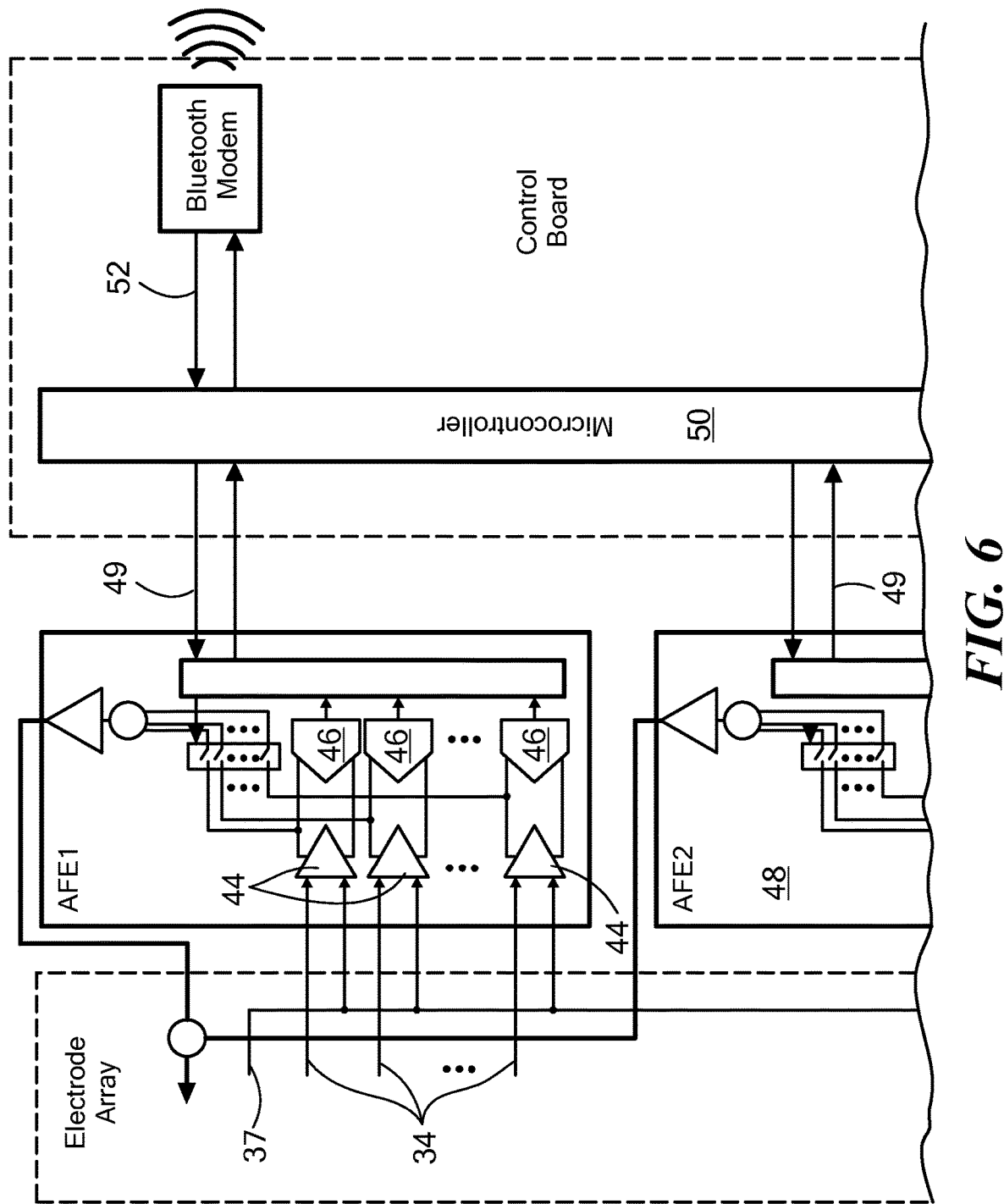
FIG. 6 is a schematic diagram of electronics in the sensor assembly.

As noted above, electronic components 42 forming the circuitry connected to the electrodes are located within the housing. In particular, each electrode 34 is electrically connected to an associated amplifier 44. See FIG. 6. The amplifier amplifies the potential difference between its associated electrode 34 and a reference electrode. The output of each amplifier is fed into an associated analog to digital converter (ADC) 46, which in turn transmits the digital signal representative of the potential difference to a microcontroller 50 for further data processing, described further below.

In the EFEG mode, one of the electrodes in the sensor array is a reference electrode. Generally, the central electrode is selected as the reference electrode 37 to simplify the geometrical considerations, but any other electrode could be selected instead. The potentials on the remaining N−1 electrodes are measured with reference to the reference electrode by the associated amplifiers. In this way, local electric field components can be estimated via local gradients of the potential.

In the EEG mode, the reference electrode can be a traditional EEG electrode, for example, attached at another location on the scalp or to the earlobe, or it can be an electrode on a different sensor assembly placed at a different location on the scalp.

Unlike traditional EEG sensors, the sensor assembly described herein can be used simultaneously in EEG and EFEG regimes. Both EEG and EFEG can be sampled concurrently by dynamically switching each amplifier's reference between the remote reference electrode for EEG mode and the local reference electrode for EFEG mode, for example, with a multiplexer at the inputs to the amplifiers.

The EEG regime is most useful when global activity of the brain is of interest, such as alpha rhythm. The EFEG and Laplacian regimes are most useful when estimating local brain activity in the vicinity of the sensor assembly. The Laplacian is the curvature of the potential proportional to the skull-scalp current density. Scalp electric field patterns are more focused than the corresponding EEG patterns, and, unlike EEG, EFEG is free from the ambiguity of choosing the potential reference. Laplacian patterns are even more focused, but the Laplacian measure, being the second derivative of the potential, is also more affected by the measurement noise than EFEG.

In the EFEG regime, one electrode, for example, the central electrode, is used as a local potential reference with respect to which potentials on the remaining N−1 electrodes, the active electrodes, are measured by the associated amplifiers. In this way, local electric field components can be estimated via local gradients of the potential. To calculate the two components of the electric field tangential to the scalp from the N−1 gradient measures, their weighted sum is computed as follows:

$$E_x = \frac{\sum_{i=1}^{N-1} \Delta F_i \cdot r_i^2}{\sum_{i=1}^{N-1} x_i^2}$$

where $F_i$ stands for the potential signal from the i-th electrode and $\Delta F_i$ stands for the (amplified) potential difference between the i-th electrode sensor and the reference electrode. N is the number of electrodes and $x_i$ stands for the x-coordinate of the electrode with respect to the center of the array. An analogous formula gives the y-component of the field. A radial component can be similarly measured if desired, but is generally not necessary, as the tangential components are dominant. If a different electrode is the reference electrode, the equations can be appropriately weighted to reflect the geometry of the location of the reference electrode.

In EEG mode, the amplified EEG potentials are averaged by the sensor assembly:

$$V = \frac{\sum_{i=1}^{N} F_i}{N}$$

where $F_i$ stands for the potential signal from the i-th electrode in reference to the first electrode, and N is the number of electrodes.

Similarly, in the Laplacian regime, the curvature L of the potential proportional to the skull-scalp current density is computed as follows:

$$L = 2 \frac{\sum_{i=1}^{N-1} \Delta F_i \cdot r_i^2}{\sum_{i=1}^{N-1} r_i^4}$$

where $r_i$ stands for the distance from the electrode to the center of the array.

The calculations implement optimal probability summation, in which each electrode's signal is weighted by the inverse of its noise variance, thus achieving the highest possible SNR. The resulting SNR increase compared to a single EFEG channel implemented as a bipolar EEG pair is given by $\sqrt{(N-3)}$ for EFEG and $\sqrt{(N-1)}$ for the Laplacian. For example, for a sensor array with 19 electrodes, the SNR increase for EFEG is $\sqrt{(19-3)}=\sqrt{16}=4$. For the Laplacian, the SNR increase=$\sqrt{(19-1)}=\sqrt{18}\approx4.243$. For EEG, assuming independent amplifier noise, the expected increase in SNR compared to a single amplifier channel is given by $\sqrt{N}$. For example, for a sensor assembly having 19 electrodes, the SNR=$\sqrt{19}\approx4.559$.

The sensor system can employ additional techniques to improve the SNR. Active amplifiers greatly improve the signal quality by reducing the capacitive coupling between an output cable and the possible sources of interference. For active amplification to work efficiently, the amplifiers need to be as close to the sensors as possible. The first stage amplification is done using active amplifiers 44 that are mounted close to the sensors, within the sensor assembly 20. In particular, the electrodes 34 are fixed within through holes in the support plate 36 and are connected very closely to their associated amplifiers 44, which are disposed on a chip that is also supported on the second side of the support plate. See FIG. 1.

In one embodiment, one or more ADS1298 or ADS1299 chips 48 commercially available from Texas Instruments can be used. These chips are multichannel and employ simultaneous sampling, 24-bit, delta-sigma analog-to-digital converters (ADCs) with built-in programmable gain amplifiers (PGAs), internal reference, and an onboard oscillator. Each chip can provide amplification for 8 independent channels. For example, for an embodiment of the sensor assembly employing 19 electrodes, three of these chips are used, which gives 24 available independent channels. The outputs from the electrodes connect to one of the eight inputs of each of the chips. It will be appreciates that future generations of similar chips can also be used.

The ADS1298 or 1299 can sample data at 24 bits with an ADC rate of 3 bytes per sample per channel. This sampling resolution and rate are adjustable to get the highest SNR and adequate data quality. A typical point sampling rate is 1 kHz, and this gives a data sampling rate of 3 kB/s per channel. For 700 channels, this gives a data rate of 2.1 MB/s. It will be appreciated that higher rates may be achievable with other chips now or in the future.

Each chip 48 outputs the data in a digital form through its serial peripheral interface (SPI) channel 49 (channels 1, 2, and 3). To reduce common mode interference, the driven right leg (DRL) of each chip is merged into a single DRL output, and the analog differential negative inputs end up as the common reference ($V_{ref}$) input to the microprocessor. All the input signals are sampled in digital form and the information is processed in the microcontroller 50.

The microcontroller 50 can also be supported by the support plate 36 of the sensor assembly 20. It receives the output signals from the ADCs for continuous monitoring and additional signal processing. The microcontroller contains a microprocessor, input and output control, and memory (RAM, ROM, etc.) with instructions to perform signal pre-processing resulting in EFEG time-series. The sensor assembly can also include a power supply, such as a battery, for example, a lithium polymer battery. Power consumption is relatively low, generally less than 200 mW. The microcontroller and other chips can be stacked if desired to fit within a small footprint within the housing 38 of the sensor assembly 20.

The on-board microprocessor is used to compute the electric field components from the individual electrode voltages, as described above, and also can be used for more involved computations in-situ, for example, to reduce data redundancy, for example, to mitigate effects of noise through additional signal processing, and to compute the signal field strengths, before the data is communicated to a transceiver 52 for transmission to another device. If exact timing or real-time data is required, FPGAs can be used.

As one example of additional SNR improvement, the bias drive circuitry provides a path for the current (common-mode signal) from the reference and into the differential inputs of the amplifiers 44 to actively cancel electromagnetic interference (EMI) and improve the common-mode rejection. The microprocessor actively monitors each of the programmable gain amplifiers. If it senses any of the electrodes has loosened (by comparing the signal amplitude with the dynamic range), then it can dynamically open the switch of the associated amplifier and eliminate it from the closed-loop gain of the bias drive signal. This can improve the common-mode rejection of the entire sensor assembly.

Figure 1:
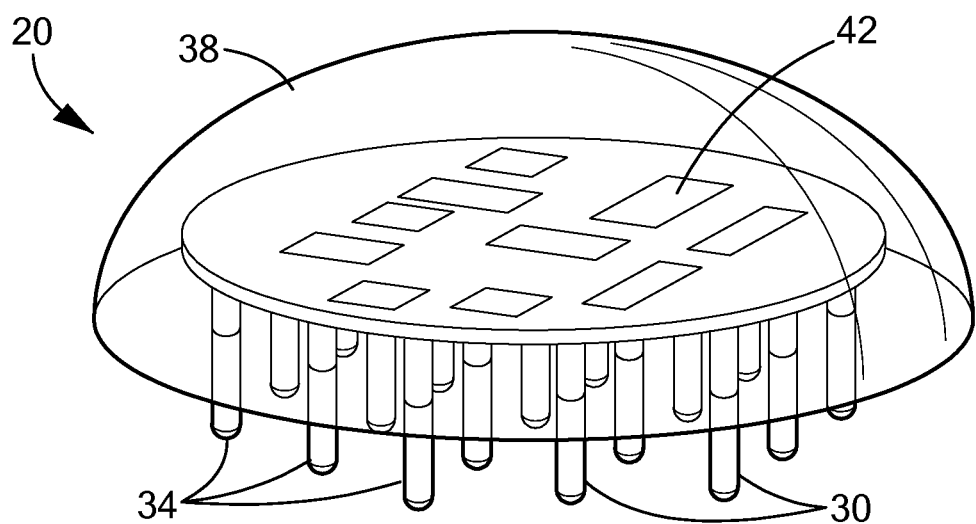
FIG. 1 is a top perspective view of a sensor assembly according to an embodiment of the invention.
Figure 2:
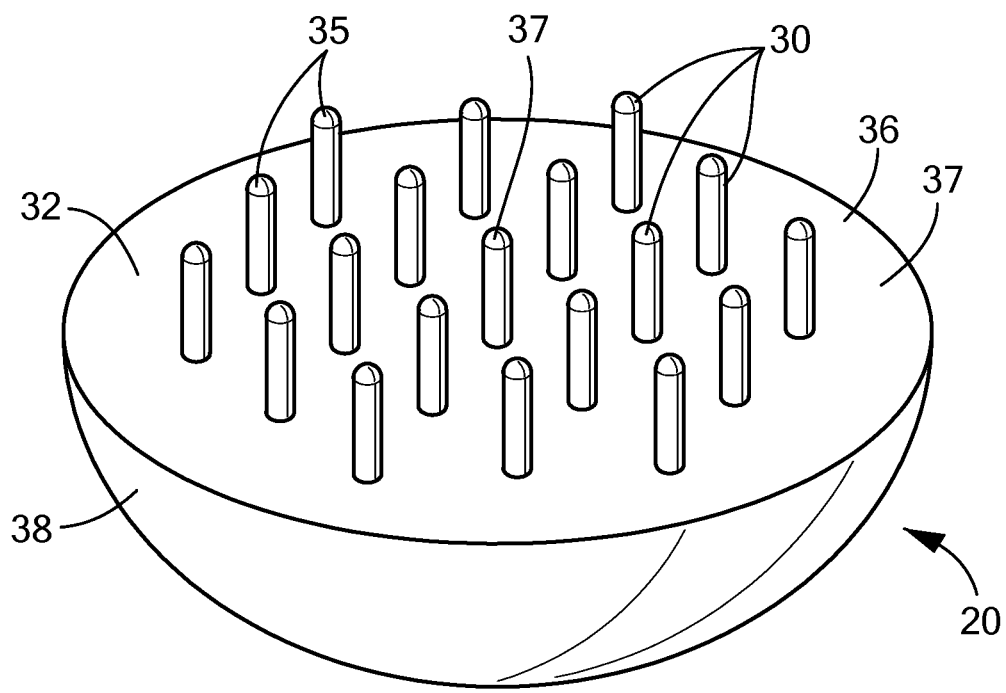
FIG. 2 is a bottom perspective view of the sensor assembly of FIG. 1.
Figure 7A:
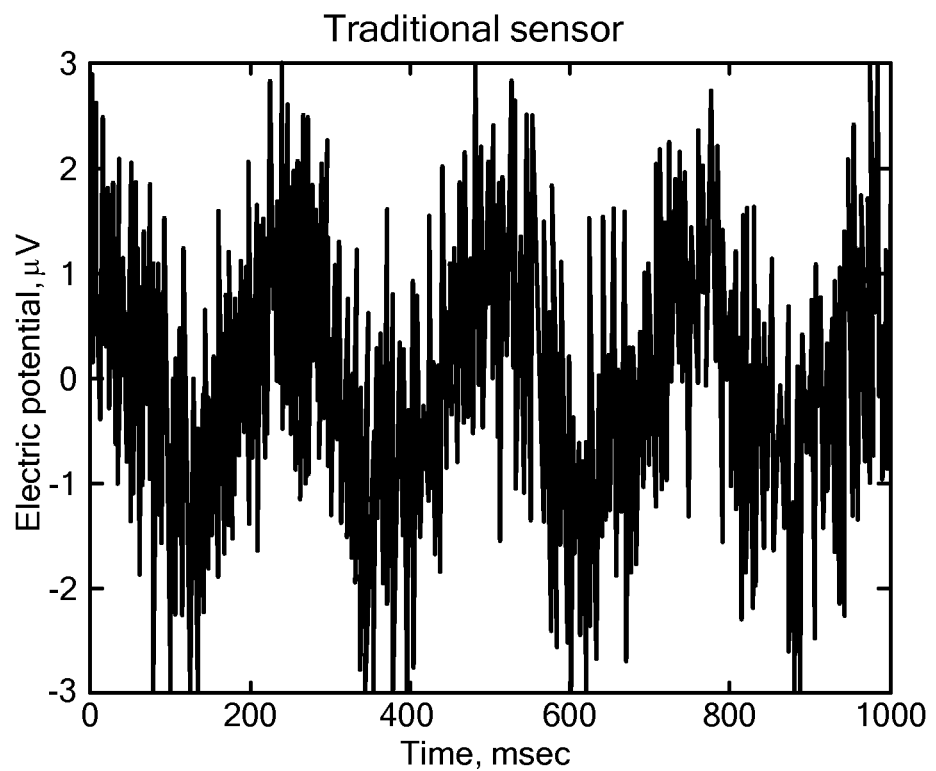
FIGS. 7A-7D are graphs illustrating the improvement in signal-to-noise ratio (SNR) of EEG and EFEG from an embodiment of a 19-pin sensor array compared to a traditional EEG sensor.
Figure 7B:
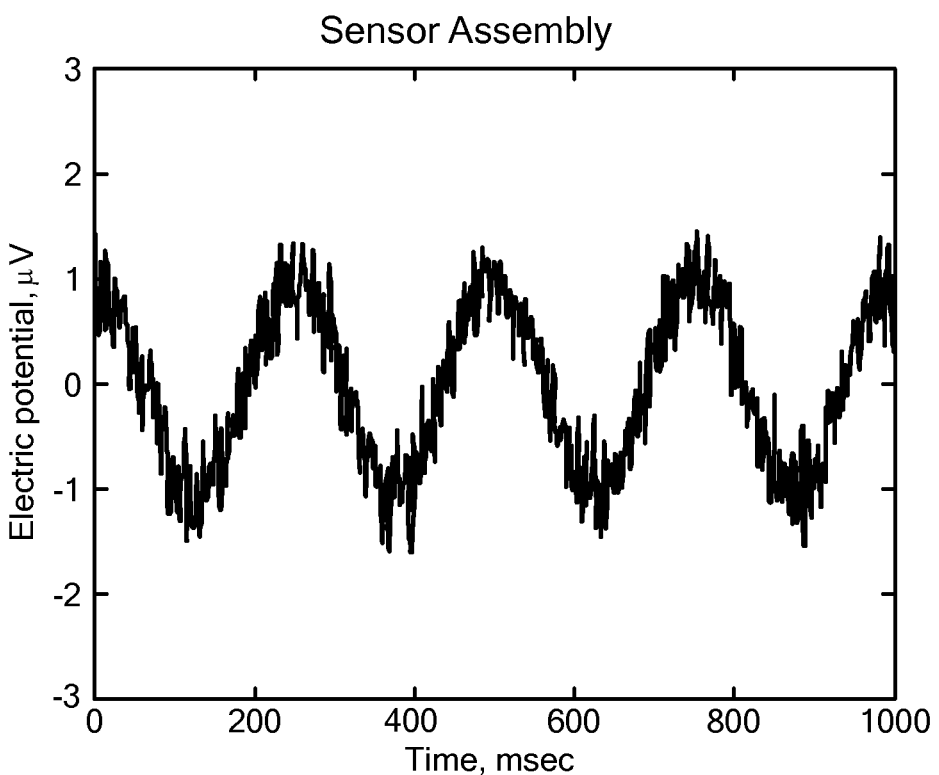
Figure 7C:
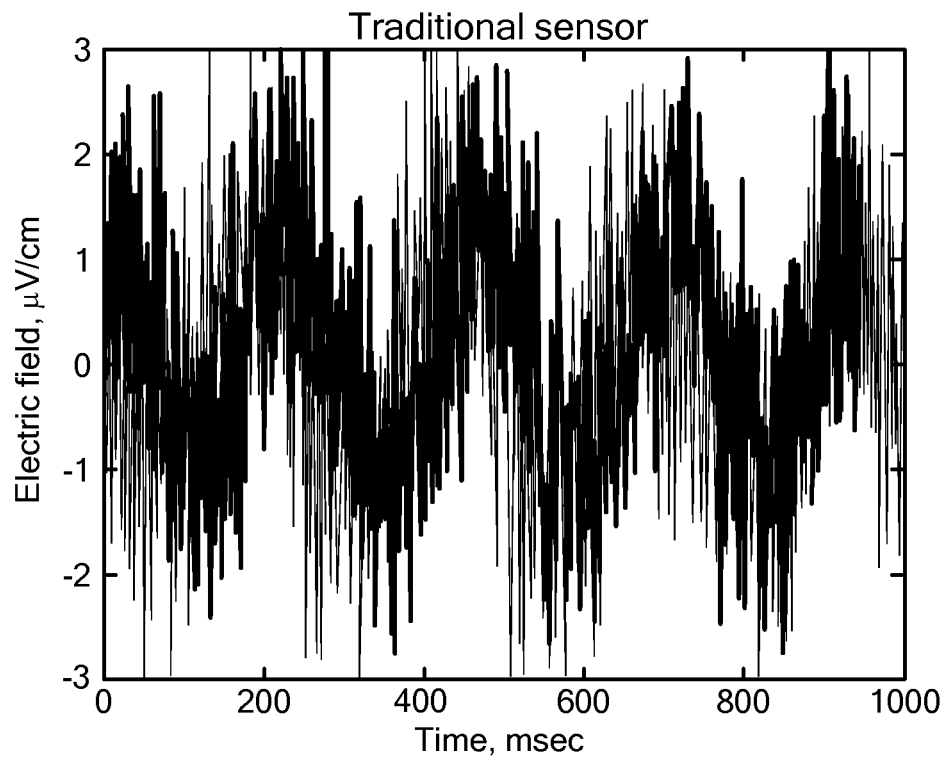
Figure 7D:
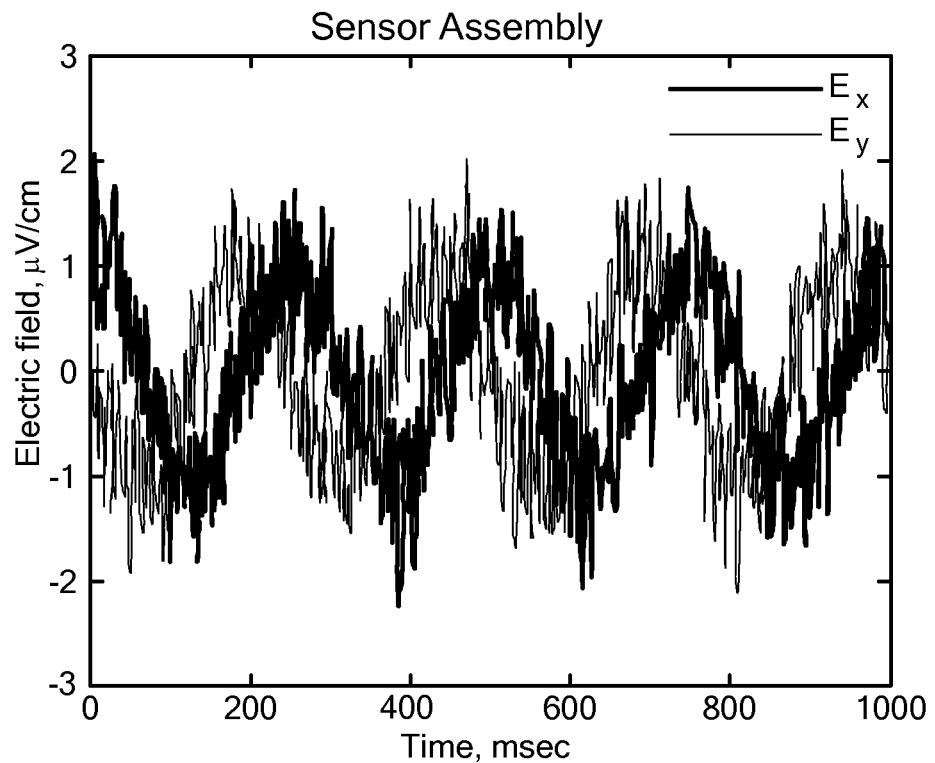

FIGS. 7A-7D illustrate SNR improvements for EEG and EFEG signals obtained in a simulation, where SNR for a single EEG channel was set to 1. The sensor array employed a 19-pin geometry as shown in FIG. 2 and a simulated electric field of a constant magnitude of 1 µV/cm rotating at 4 Hz. FIG. 7B indicates a $\sqrt{19}$ improvement in the SNR of EEG potential detected with the 19-pin sensor array over a traditional EEG in FIG. 7B. FIG. 7D indicates a 4-fold improvement in SNR for the associated electric field measurements.

Figure 8:
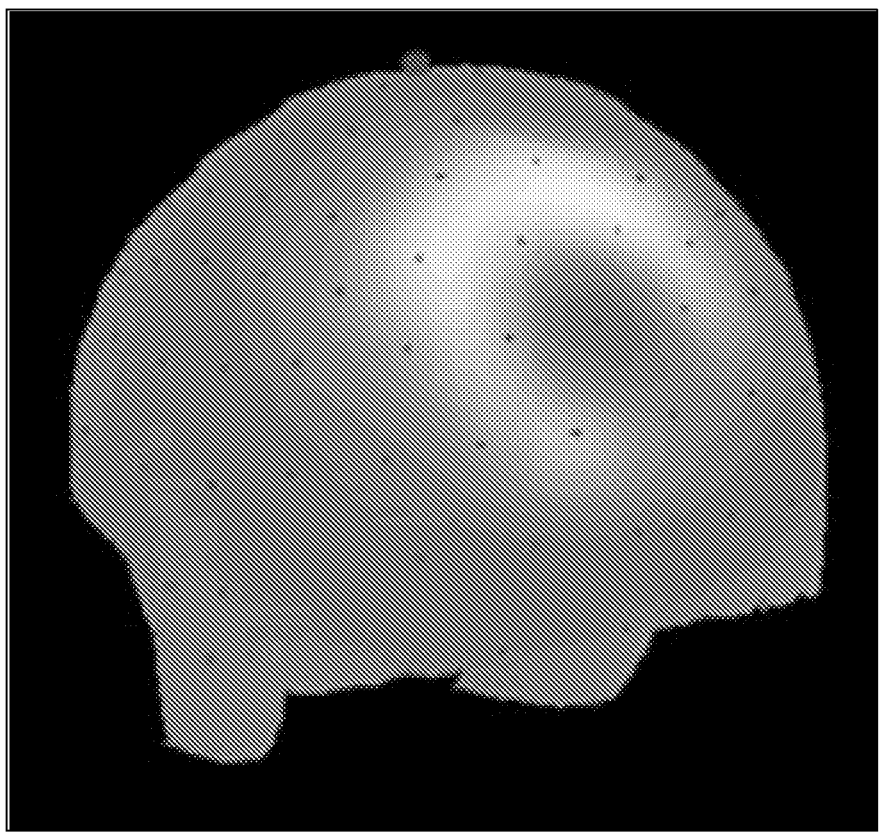
FIG. 8 is a schematic illustration of an image of brain activity generated from EFEG data obtained from a sensor assembly.

From the measured electric field and potential data, an estimate of the locations of the electric field and potential sources can be made and an image of brain activity can be generated. Various algorithms and head models to estimate the locations from the data and to generate brain activity images and image maps can be used. For example, FIG. 8 is a schematic illustration of an image of brain activity generated using a software suite known as Harmony. See Petrov, Y., Harmony: EEG/MEG Linear Inverse Source Reconstruction in the Anatomical Basis of Spherical Harmonics. PLOS ONE, October 2012, Vol. 7, Issue 10, e44439.

Example

An embodiment of a sensor assembly was tested to determine if EFEG provides additional information on brain activity compared to conventional and high-density EEG, and to determine if the closer electrode spacing, that is, an ultra-dense electrode density, within the sensor assembly is capable of providing additional EEG information compared to the sensor spacing or electrode density of traditional and high-density EEG.

In particular, a sensor array with an ultra-dense array of electrodes was used in which a square 4×4 grid of small diameter electrodes had an inter-electrode separation of 1 cm, or a density of 1.0 $cm^{-2}$. For comparison with existing high-density EEG systems, the electrode density of several 128-sensor EEG nets from Electrical Geodesics Inc. was estimated as 0.167 $cm^{-2}$. The electrode density of EEG nets with 64 sensors was estimated to be 0.084 $cm^{-2}$; and the electrode density of a net with 256 sensors, currently the densest EEG nets commercially available, was estimated to be 0.269 $cm^{-2}$.

The approach used a signal classification paradigm in which a classification algorithm was used to carry out binary classification of individual trials based on their EEG data. It was hypothesized that the amount of functional information I captured by the array is a monotonically increasing function of the algorithm's classification accuracy $p_c$. The advantage of this approach is that (i) it gives an estimate of functional brain information compared to mere spatial variation of EEG, and (ii) given a "hotspot" of the functional information relevant to the classification task on the scalp, it is sufficient to estimate I at this location as a function of sensor density, I(d), to obtain a reliable estimate of the full-scalp I(n).

In this paradigm, eleven subjects viewed images of words presented one by one on a computer monitor. On each trial, a word appeared on the screen for half a second followed by a blank screen for another half a second The words displayed were of two types: common English nouns printed in capitals, such as TABLE, and "Hebrew" words: nonsense words produced by substituting Latin characters in the English words with Hebrew characters with the same ASCII codes. The subjects were either native speakers or fluent speakers of English. The subjects did not speak or read Hebrew and were not familiar with the Hebrew alphabet. Over the course of a ten-minute long EEG session, each subject viewed 236 different words of each type randomly interleaved. The timing of the presentation of the words was correlated with the timing of the data gathered from the electrodes, so that the brain response could be correlated with each word presentation.

In a preliminary experiment, a common "informative" location was chosen in the parieto-occipital scalp region, approximately 6 cm above and left of the inion. The 4×4 ultra-dense sensor array was applied to this location for all subjects. Recorded visually evoked potential (VEP) epochs were separated into two sets, English and Hebrew, based on which stimulus was presented in a given epoch. Part of the data was used for training a classification algorithm, while the remaining data were used for testing the performance of the trained algorithm, using the Naïve Bayes approach.

Figures 9, 10:
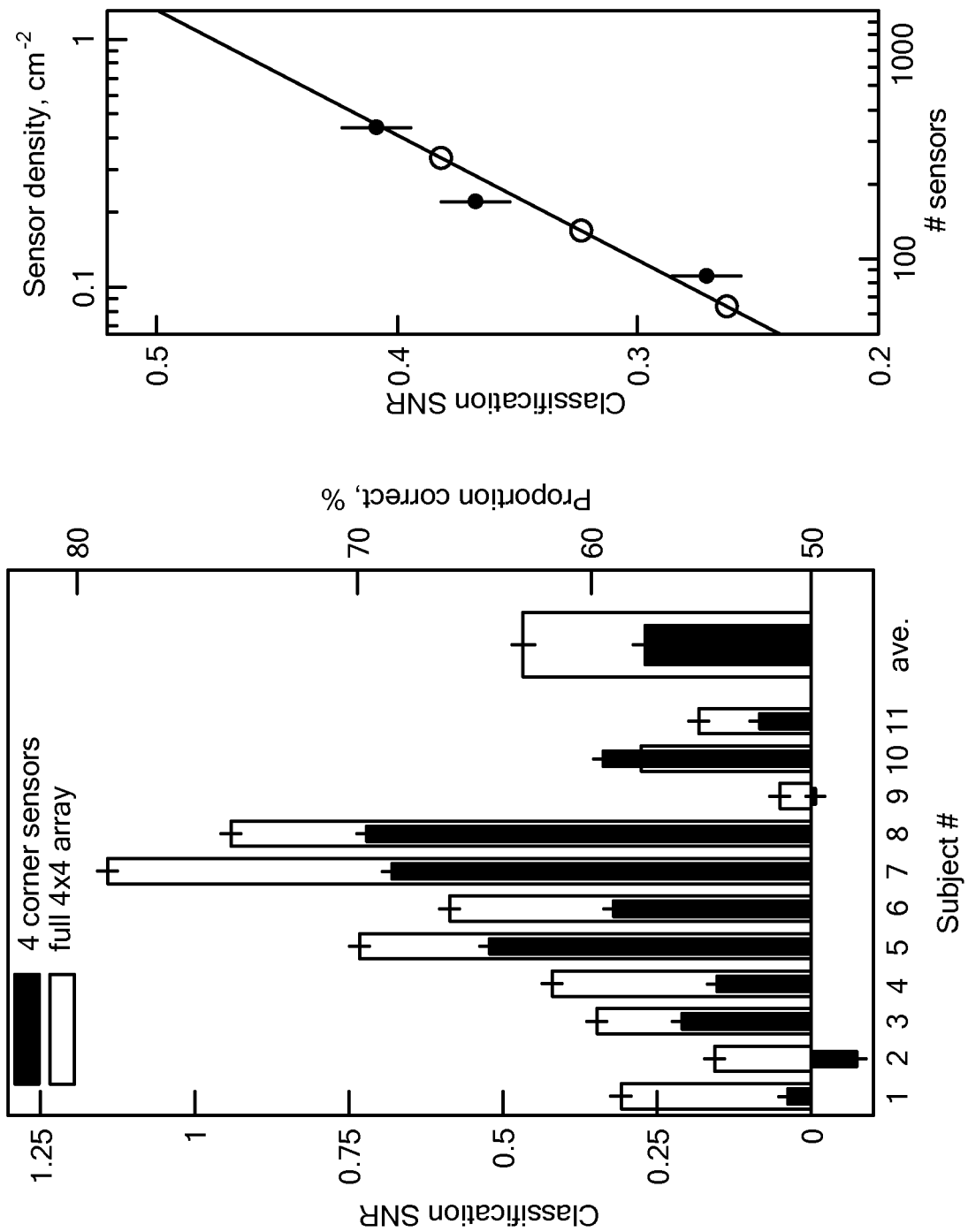
FIG. 9 is a graph of a proportion of correct classifications and corresponding signal-to-noise ratio (SNR) from an experiment testing a 4×4 sensor array.
FIG. 10 is a graph of SNR as a function of sensor density.

The percentage of correctly classified trials ($p_c$) varied among subjects from 52% to 78%. The percent correct values were converted to d' values, i.e., to the signal-to-noise ratio (SNR) of the classification analysis using d'=2 norminv ($p_c$), where norminv( ) stands for inverse of the cumulative density function (cdf) for normal distribution with zero mean and unit variance. The SNR and $p_c$ for each subject are plotted along the y-axes in FIG. 9; error bars show one standard deviation. When all 16 electrodes (full 4×4 array) were used, the SNR was 0.47±0.02 on average. When only the 4 corner electrodes of the array were used for the same analysis, the average SNR dropped to 0.27±0.02. Hence, sampling EEG at 1 cm scale on average offers almost twice the amount of functional brain signals as compared to sampling at 3 cm scale. Individually, the improvement was significant for 10 of the 11 subjects. The corner electrodes, at 0.11 cm$^{-2}$ sensor density, emulate a full-scalp EEG array with approximately 84 sensors. This is comparable with the 64- and 128-sensor high-density EEG systems most common today. The full 4×4 array, at 1 cm$^{-2}$ sensor density, emulates an ultra-dense EEG scalp array with 766 sensors. SNR for two intermediate sensor densities was estimated by interpolating the 4×4 array data to square arrays with 5 and 9 electrodes, thus emulating full-scalp EEG arrays of 168 and 336 sensors respectively. SNR as a function of the sensor density grew approximately logarithmically (FIG. 10). An adequate fit ($\chi^2$=3.69, p<0.3) was obtained by linear least squares and is given by the following formula:

SNR=0.476+0.086 log(d), where d is the density of sensors: 0.11, 0.22, 0.44, and 1 cm$^{-2}$ for 4, 5, 9, and 16-electrode ultra-dense EEG array configurations, respectively.

Figure 11:
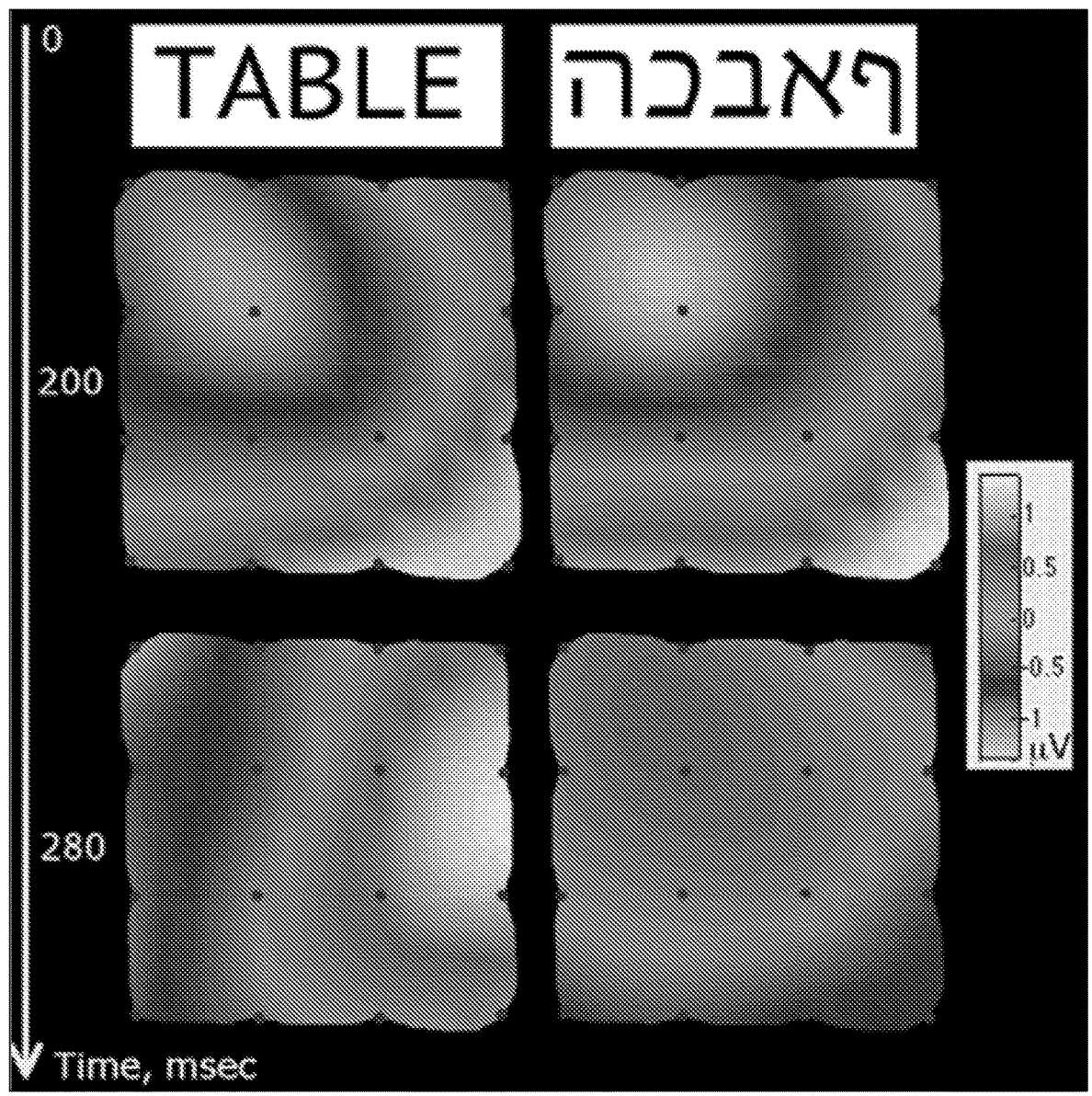
FIG. 11 illustrates an example from one subject of visually evokes responses averaged over epochs across an ultra-dense EEG array.
Figure 12:
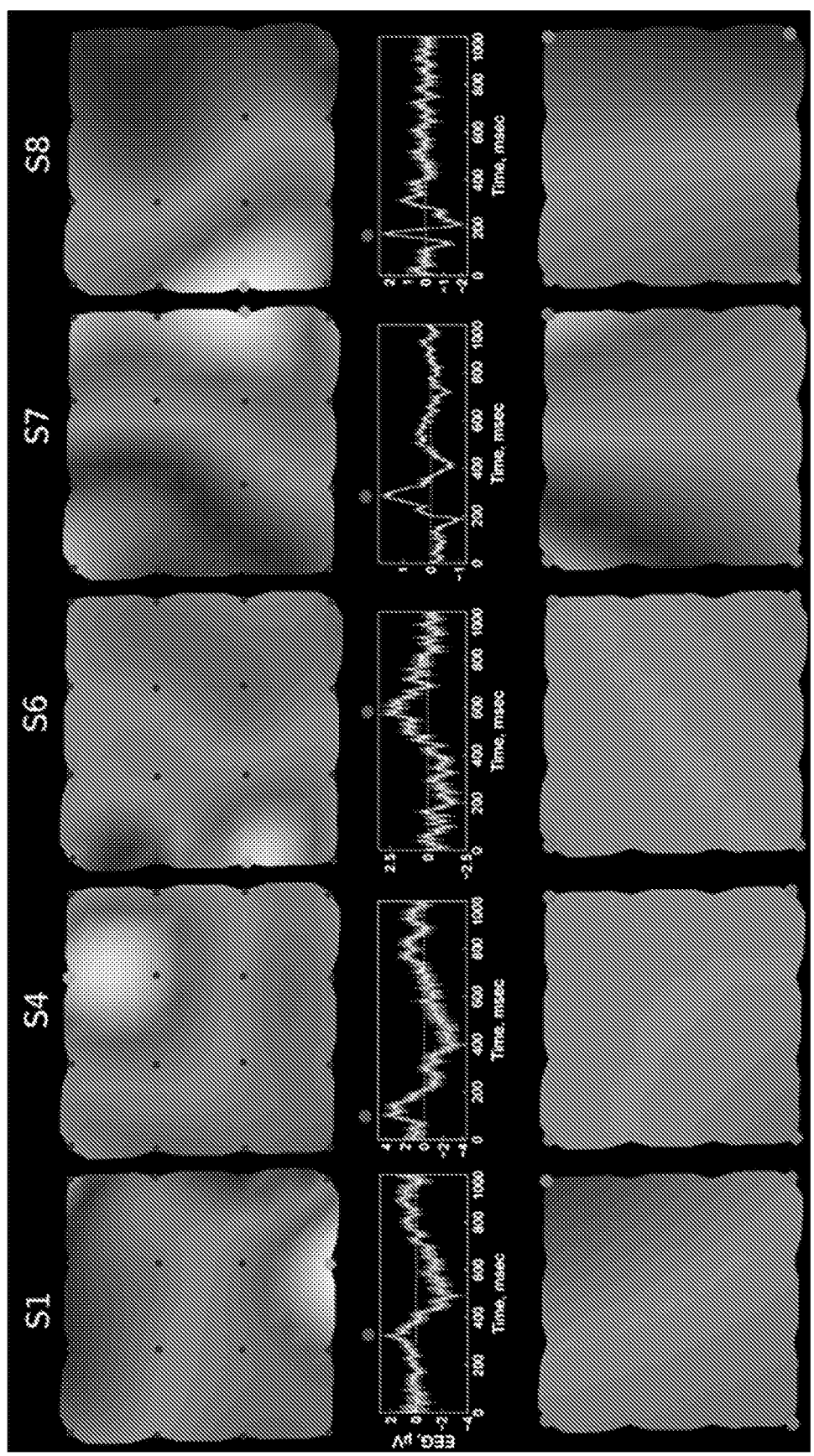
FIG. 12 illustrates in the top panel, snapshots of dVEP variation across an ultra-dense EEG array for five subjects; in the middle panel, a time course of an electrode closest to a hotspot, and in the bottom panel, snapshots of dVEPs interpolated using only the corner electrodes.

To understand the SNR increase due to the ultra-dense EEG sampling, the spatial distribution of the evoked responses was examined. VEPs for a representative subject are shown in FIG. 11. Data were averaged over stimulation epochs, interpolated between electrodes in the 4×4 array, shown here by a varying grayscale, although usually represented by color maps. The electrode locations are marked by black dots. Responses to English and Hebrew stimuli are shown on the left and right respectively. Snapshots for the two time points, as indicated by the time arrow, demonstrate functional variation of the responses between the two conditions: while evoked responses were alike at 200 ms from the stimulus onset, they became quite different 80 ms later. The VEP differences between English and Hebrew stimuli, dVEP=VEP$_{English}$-VEP$_{Hebrew}$, are shown in the top panel of FIG. 12 for the five subjects with the strongest effects of electrode density on the classification accuracy. The dVEP time course of the electrode with the largest observed dVEP is plotted below each snapshot. The dot above each plot indicates when the corresponding snapshot was taken. The observed dVEP variations across the ultra-dense EEG array are highly significant and formed local hotspots: the potential variations between English and Hebrew stimuli were as high as 2 µV/cm for some subjects. Time courses of the hotspots have well-defined peaks. This indicates that the hotspots reflect evoked brain responses rather than measurement-related noise. The hotspots are made particularly conspicuous by their absence in dVEPs interpolated using corner electrodes only. This is shown in the bottom panel of FIG. 12. Note also that the shown data reflects local variation of VEP measured with respect to the array's average and thus may look different from conventional VEPs recorded using global reference.

The observed classification SNR improvement of ultra dense EEG on high density EEG may result from: (i) an increased number of independent signals, as reflected by the dVEP hotspots in FIG. 12, or (ii) decreased noise due to noise averaging among nearby ultra dense EEG electrodes. In order to test this latter mechanism, the classification analysis was repeated while limiting the number of classifiers to the single most informative electrode. This precluded any noise averaging between nearby electrodes. The average SNR for the full 4×4 array dropped from 0.47±0.02 to 0.25±0.02, but the 4-corner SNR decreased proportionally from 0.27±0.02 to 0.15±0.02. This demonstrates that noise averaging cannot explain the observed improvement in classification accuracy.

One could also argue that the improvement might be due to some artifact of the classification algorithm benefiting from a larger number of input signals, even if the number of independent signals remained constant (i.e., when VEP is oversampled). The "most informative electrode" analysis described above also applies here to refute this argument, since only one electrode was used in both cases. However, a more straightforward test was also carried out, in which raw VEP data on the corner electrodes was interpolated over the remaining 12 electrodes of the 4×4 array and the classification analysis was applied to the interpolated 16-electrode data set. There was no significant increase in average classification accuracy across subjects between the interpolated 4×4 dataset ($p_c$=0.58±0.04). Hence, the higher classification accuracy for the full 4×4 array appears to be a genuine advantage of sampling EEG at 1 cm resolution.

Figure 13:
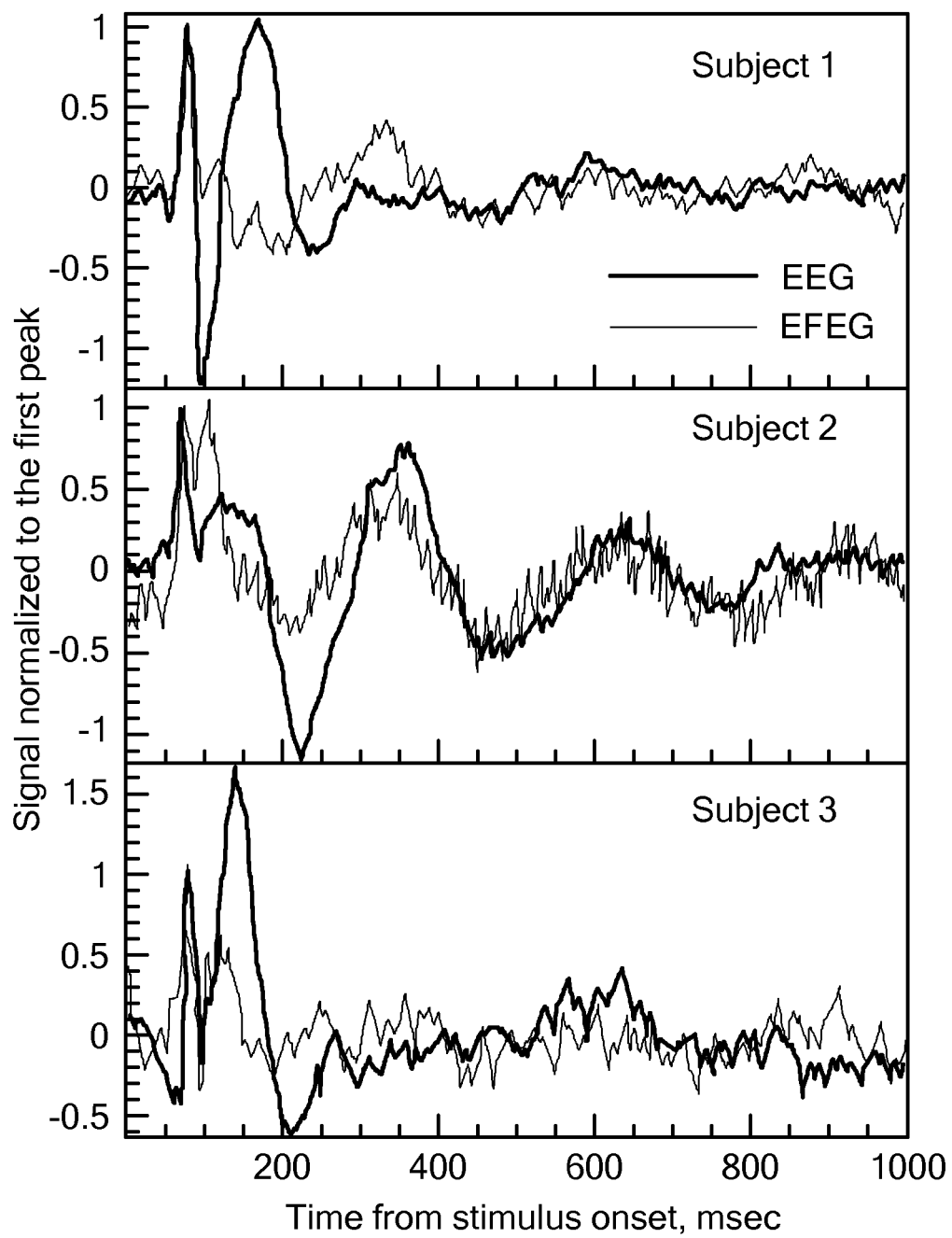
FIG. 13 are graphs of an EEG signal and an EFEG signal over time from an embodiment of a sensor array tested on three subjects.
Figure 14A:
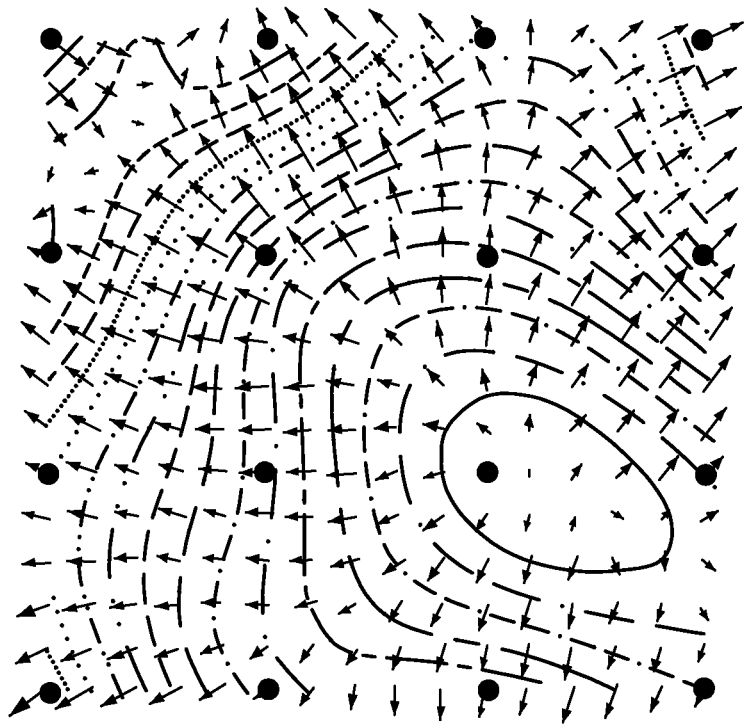
FIGS. 14A and 14B are maps of EFEG signals of electric fields from a local area of a brain obtained during testing of an embodiment of a sensor array.
Figure 14B:
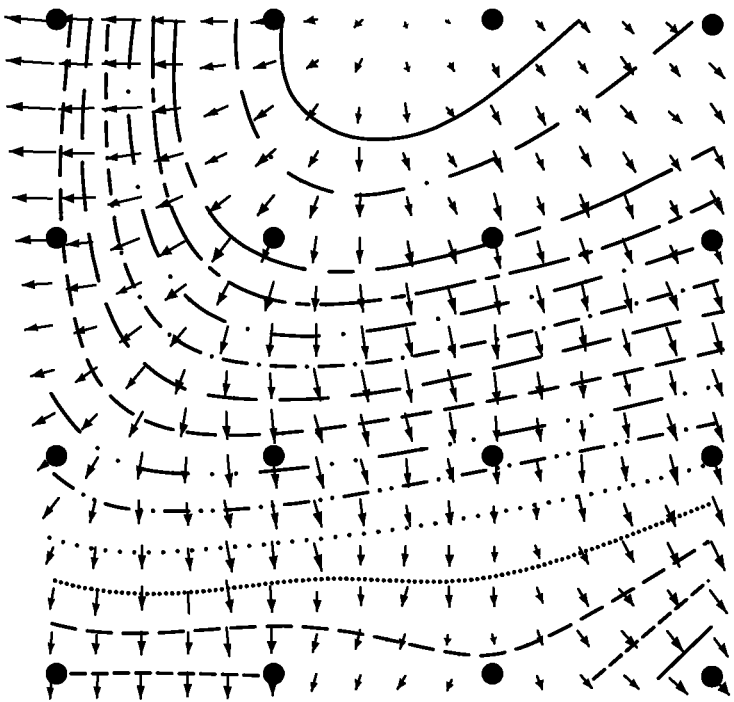

Further, FIG. 13 illustrates the measured EFEG and EEG at one location within the brain for three of the subjects, indicating that EFEG provides information in addition to that provided by EEG. The spatial variation of the potentials and the fields are shown in FIG. 14A for an English stimulus and in FIG. 14B for a Hebrew stimulus.

This study demonstrates that the high spatial frequency variations of electric potential captured by ultra-dense EEG provide practically significant information on brain states. The observed twofold improvement in the SNR of the classification paradigm is immediately relatable to many brain computer interface (BCI) applications. Similarly, significant improvements may be expected for the localization of EEG sources. This study also shows that EFEG provides additional useful information beyond the information provided from EEG alone.

Figure 15:
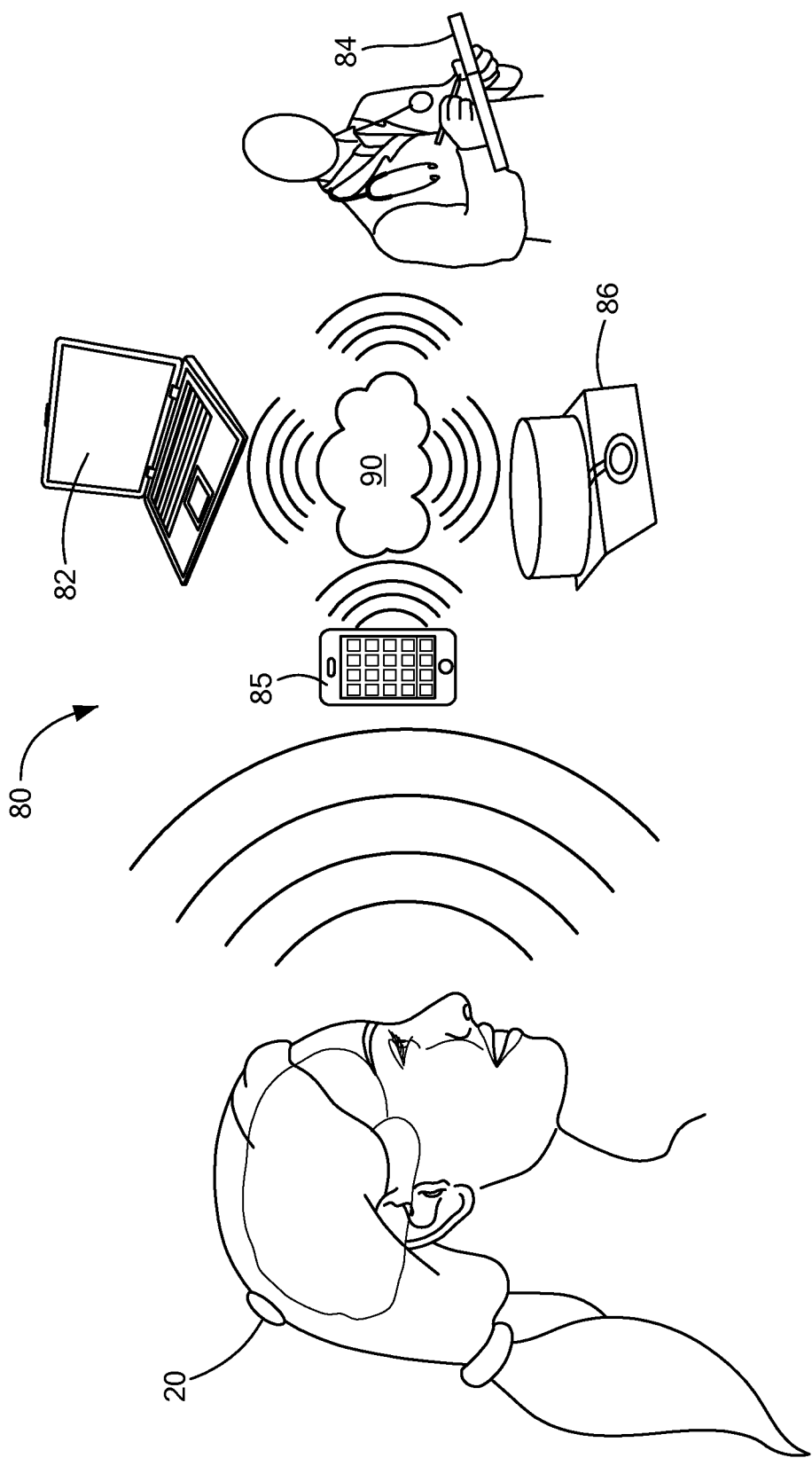
FIG. 15 is a schematic illustration of an embodiment of a sensor assembly in wireless communication with a network of devices.

One or more of the sensor assemblies as described herein can be part of a sensor system. Referring to FIG. 15, the data for a sensor assembly 20 can be transmitted to a peripheral device for further analysis. Transmission of signals from the sensor assembly can be wired or wireless, for example, via connection standards such as Bluetooth, Zigbee, WiFi, 802.15.4, WLAN, RFID and other wireless standards. With a wireless system, AC noise can be reduced further, because a length of cable is eliminated. The output data can be saved locally on a flash drive continuously and can be transmitted to a host system or cloud storage wirelessly in real time with certain latency.

In one embodiment, a sensor system 80 is provided in which one or more the sensor assemblies can communicate with a device 85 such as a smartphone, tablet computer, laptop computer, or other device. The device 85 can in turn transmit the data to another host system, for example, via the internet 90. For example, the sensor assembly can transmit data wirelessly to the subject's smartphone, which can in turn transmit the data to another external computer 82, a processor device 84 employed by a physician, clinician, or researcher, or another networked facility 86 located remotely from the subject. Thus, the subject can be continuously monitored in a location, such as his or her home, that is remote from a hospital or other medical facility or a laboratory. For example, an epilepsy patient can be continuously monitored for signals indicative of an epileptic seizure while maintaining a normal routine at home, rather than being admitted to a hospital for such continuous monitoring. Messages from the clinician can be transmitted back to the subject as necessary.

The data from the sensor system 80 can be used by, for example, a trained researcher conducting investigations into brain electromagnetic activity or a clinician diagnosing neurological conditions. The system can be used to diagnose and treat animals, including mammals and, in one embodiment, human subjects. For example, the system can be used for functional brain imaging at high temporal and spatial resolution, for pattern recognition and cognition, or for comparing the brain activity of a subject to the brain activity of a normal subject or to a database of the brain activity of many subjects. The system can be used to investigate neural correlates of vision and speech, aging, sleep, or diseases such as epilepsy, Alzheimer's disease, Parkinson's disease, amyotrophic lateral sclerosis (ALS), stroke, autism, depression, and traumatic brain injury. For example, the data can be analyzed for source localization for epilepsy or for detecting correlations between EFEG and EEG patterns with seizures or silent events. As another example, the system can be used to detect correlations between gait and attention in movement disorders during the aging process and/or in Parkinson's disease. The system can be used during movement rehabilitation of stroke patients, for patient-driven neurorehabilitation, mobile brain/body imaging, gait research and gait rehabilitation and neuroergonomics.

The system can be used for investigating or utilizing human-machine and brain-computer interfaces. Currently, brain-computer interfaces require an active stimulus, often in the form of a flickering pattern, which the user is expected to focus on for extended durations of time. The sensor array, in contrast, directly picks up and transmits in real time the brain activities of the subject in normal settings, without the need for specialized equipment. For example, signals from a sensor array can be transmitted to a host processor and used to control an external device, for example, to turn a device on or off, move a cursor, control the volume of an audio output, control a prosthetic device, control a wheel chair, control a speech synthesizer, make a phone call, or provide a sound or vibration to awaken a sleepy driver. The host processor can make a comparison of the transmitted signals representative of an emotion or an intentional thought with a database, look-up table, or brain map. A training regimen can be performed by which a user can learn use of brain activity to control a device.

Figure 16:
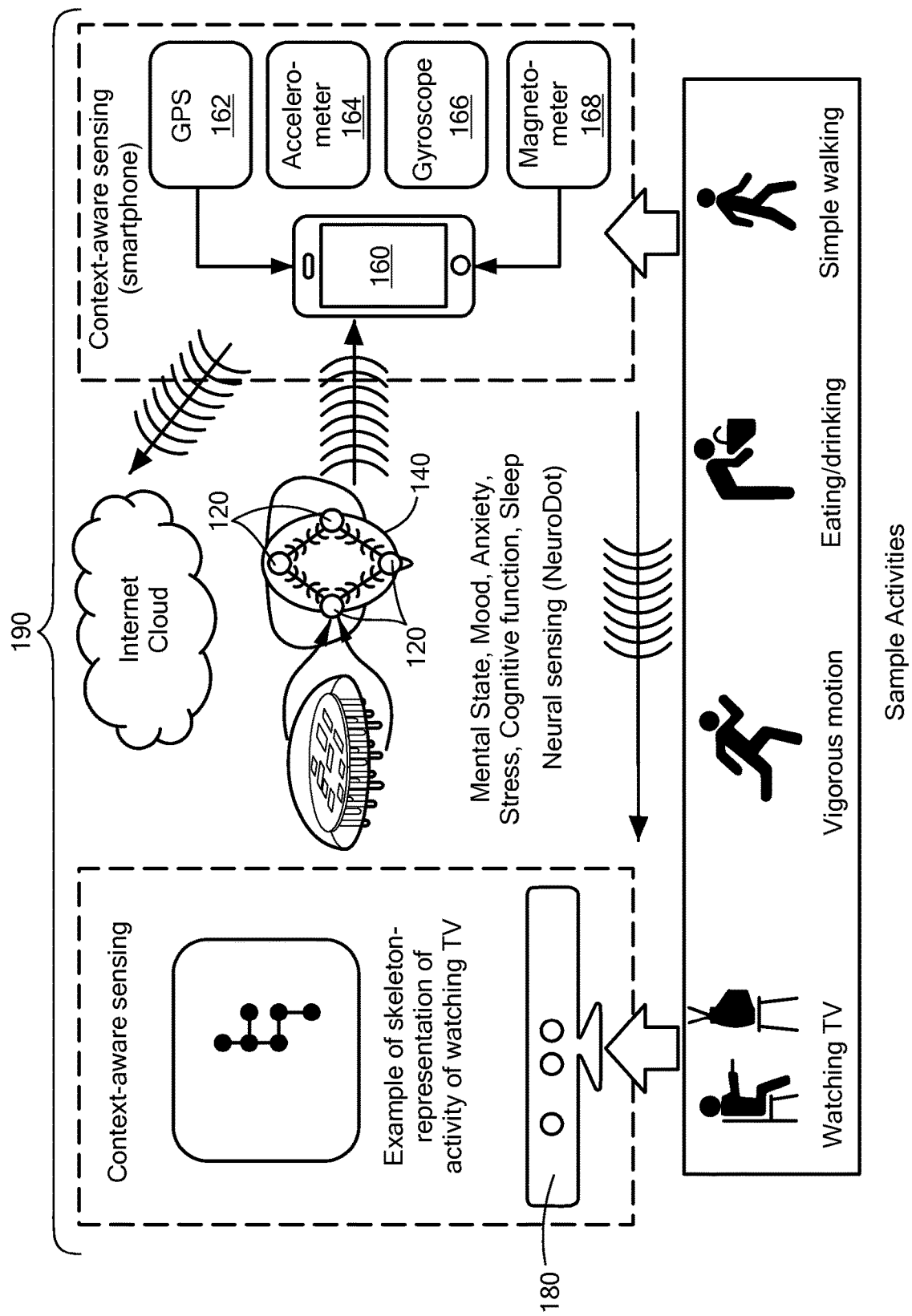
FIG. 16 is a schematic illustration of an embodiment of several sensor assemblies in a medical body area network.

In one embodiment, a sensor system can include one or several sensor assemblies 120 worn by a subject 140 to gather brain activity data. See FIG. 16. Other sensors that currently exist within a smartphone 160, such as a GPS device 162, an accelerometer 164, a gyroscope 166, and a magnetometer 168, can be used to provide context data when the smartphone is worn or carried by the subject. (It will be appreciated that such sensors can be provided on any other form of wearable device in addition to a smartphone and references to a smartphone herein can include any such other device.) Other devices 180 that use cameras and microphones to capture movement and speech of a subject can be used to provide context data as well. These sensors and devices can be integrated into a medical body area network 190 (MBAN) for the subject 140. Data from the brain activity sensor assemblies can be synchronized with data from the other sensors and devices that provide context, so that the subject's brain activity can be associated with the activity that the subject is performing. In this way, factors that trigger a particular neurological state, such as mood, anxiety, stress, cognitive functioning, or sleep, may be identified, which may help in recommending treatment.

Figure 17:
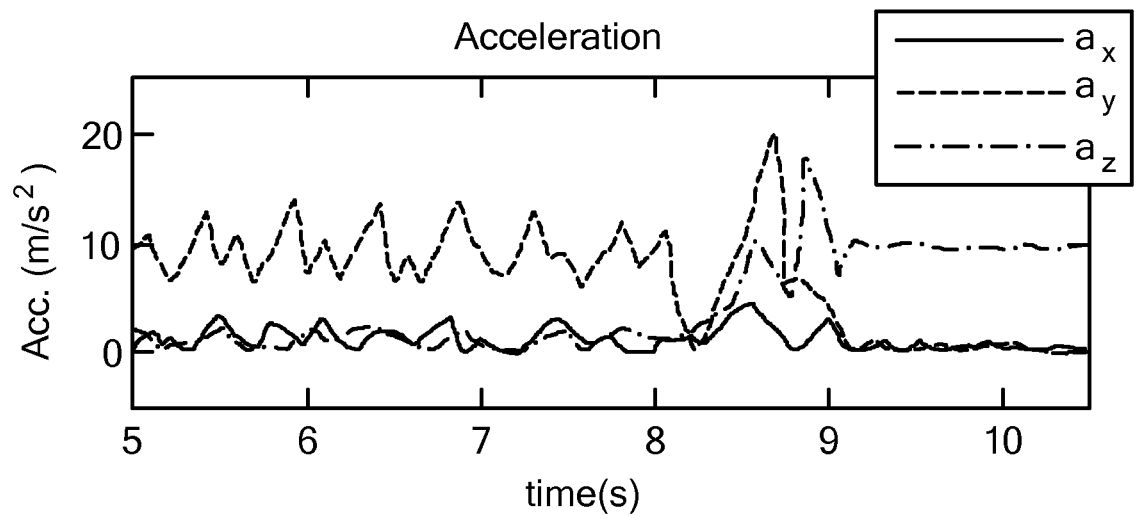
FIG. 17 is a graph of acceleration over time from a smartphone accelerometer showing a sudden fluctuation indicating a potential fall.
Figure 18:
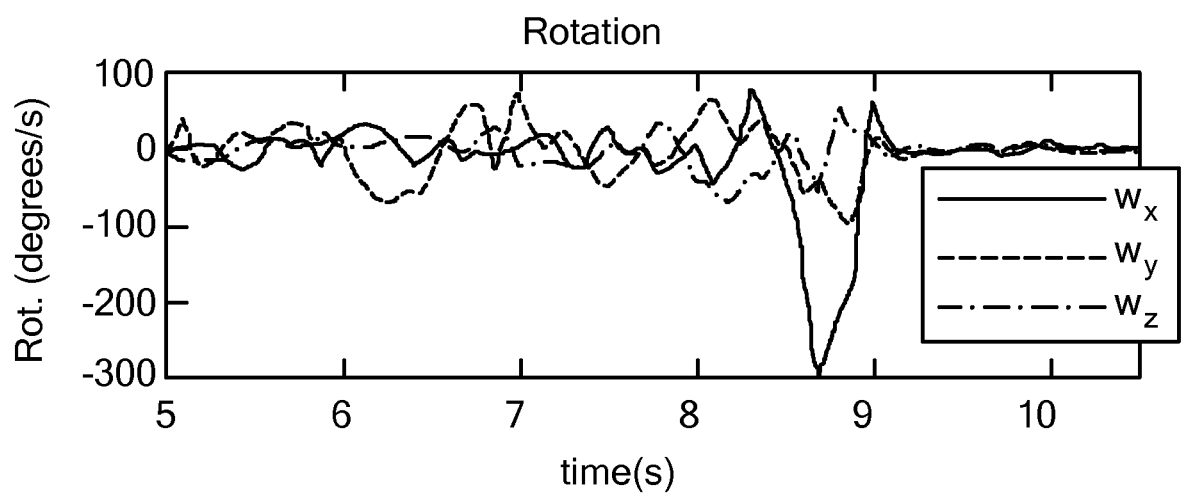
FIG. 18 is a graph of rotation over time of a smartphone showing a sudden fluctuation indicating a potential fall.

For example, sudden falls can potentially indicate serious problems, such as Parkinson's disease, cognitive problems, dementia, or the onset of a stroke. Sensors on a smartphone can collect data on acceleration, linear acceleration, angular velocity and orientation when a subject who is walking normally suddenly falls. In particular, a total acceleration can be calculated from the accelerations in three orthogonal axes. FIGS. 17 and 18 show the acceleration, linear acceleration, angular velocity and orientation data collected by a smartphone when a person is walking normally but suddenly falls down. The accelerations in all three axes are combined to find the total acceleration:

$$|A_T|=(a^2_x+a^2_y+a^2_z)^{1/2}$$

The individual traces are shown in FIG. 17. The angular velocity can be collected using the hardware-based tri-axial gyroscope. A smartphone's coordinate system is defined relative to the phone and the axes remain static throughout. That is, the axes are not appropriately rotated when the smartphone's orientation changes. Thus, the geometric mean value is more useful and can be calculated from the velocities in three orthogonal directions:

$$|w_T|=(w^2_x+w^2_y+w^2_z)^{1/2}$$

Figure 19:
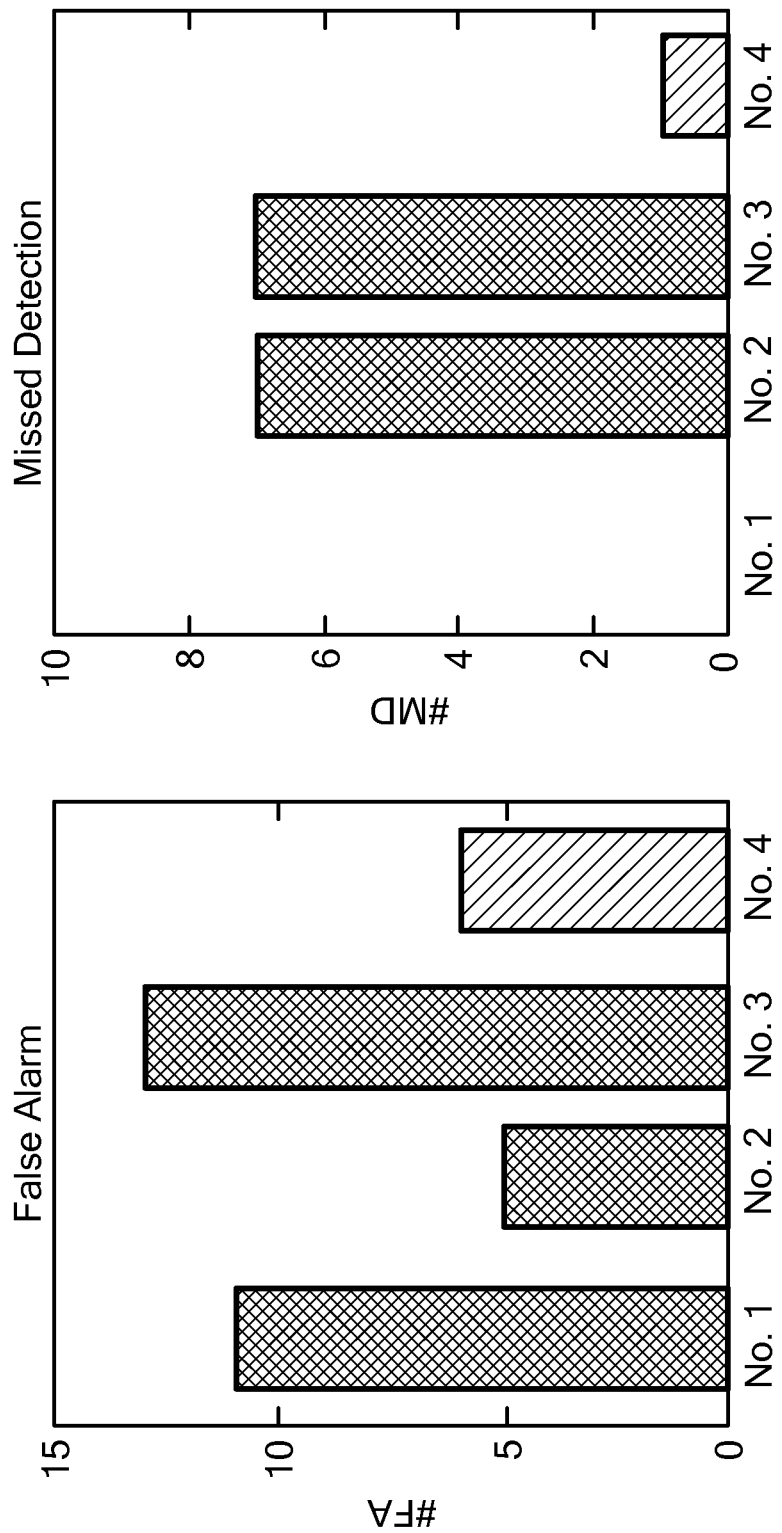
FIG. 19 is a graph comparing a fall detection technique of the present invention to three other fall detection apps, showing the number of false alarms and the number of missed detections.

The traces are shown in FIG. 18. Similarly, the orientation of the phone is determined by the azimuth, the pitch (the angle around one axis, e.g., the x-axis) and the roll (the angle around another axis, e.g., the z-axis). A fall detection technique compares the total acceleration against an empirically measured threshold obtained from multiple subjects and checks if the rotation sensor registers a simultaneous change of more than 90°. Coordinating the fall data with the subject's electromagnetic brain activity may lead to an evaluation of the cause of the fall and possibly a diagnosis and course of treatment. The present fall detection technique has been found to result in lower false alarms and missed detection errors compared to other commercially available apps, as shown in FIGS. 19A and 19B. In these figures, Nos. 1, 2, and 3 represent commercially available smartphone fall detection apps. No. 4 represents the present fall detection technique described above. The data analysis can occur on the smartphone, or the smart phone can transmit the data to another computer for analysis. When the detected context is the action of the user falling down, it may indicate an urgent notification event. For example, the data collection from the sensor array and the event of the fall, when taken together, may point to a possibility of a stroke. Thus, the data are immediately transmitted by the smartphone to alert necessary caregivers.

The system can include a database of sensor readings that are indicative of particular activities, such as watching TV, sitting, eating, walking, or exercising. As an example, simple daily activities, such as watching TV, may introduce temporary changes in the stress level and the mental state of a subject, depending on the TV program's content. The system can include a map of the living space or other environment of the subject with coordinates of elements, such as facilities and equipment, for example, the locations of a TV, washroom, exercise machine, dining table, and the like. The assisted GPS (AGPS) capability of the smartphone can be used to determine the location of the subject within a room or within a facility. The accelerometer can be used to detect if the subject is undergoing continuous motion, suggesting a vigorous physical activity. If not, then the orientation of the smartphone and hence, the subject, with respect to the Earth's magnetic axis is determined using the smartphone's magnetometer. The point location of the AGPS as well as the orientation along the line of sight to the TV can indicate with a high probability that the subject is watching TV.

As a further example, a device that captures movement and speech of a subject, such as the KINECT®, available from Microsoft and developed initially for the gaming field, provides the capability of producing a digital representation of skeleton-figures of a subject without the privacy invasion that accompanies a visual confirmation from continuous monitoring by another person. These skeleton figures are expressed as a graph of vertices and edges that correspond to the joints and limbs of the subject under study. The device also returns information on depth estimation, which provides additional location information within the room. Using such a device, instances can be captured in which the subject does not physically change location, hence recording zero variations by the smartphone accelerometer, but still engages in limited motion that impacts the neurological data. For example, while eating, the movement of the subject's lower jaw can introduce noise into the sensed data by the sensor assembly for monitoring brain activity, which may result in a sudden spike. The skeleton figure data can be used to check if the loci of the vertex and edge movements are regular, perhaps corresponding to that of a moving arm during eating. As another example, the movement capture device can be activated if the sensors on the smartphone indicate a potential fall by the subject.

A database of patterns engaged in by the subject can be provided to establish a comprehensive context-aware framework. The smartphone can be placed in a master role to poll slave nodes, such as one or more brain activity sensor assemblies and other external devices, such as movement and sound capture devices. The smartphone can timestamp and aggregate the data from all the sources, including the sensors on board the smartphone itself. The smartphone can continuously monitor the sensor data and if deviations from a known or predicted pattern are detected, it can increase the duty cycle for the affected sensors. In some embodiments, the smartphone can send the data, for example, in a compressed format, to a host processor or to a cloud computing facility for subsequent data analysis. In other embodiments, the smartphone can transmit the data to an external computer, such as a laptop computer, for data analysis. In still further embodiments, the data processing and analysis can occur on the smartphone itself. As one example, if the data analysis on the smartphone suggests that the subject may have fallen, the smartphone can activate a movement capture device and/or transmit an alert to other personnel for a visual check.

Experiments have also been undertaken to determine the latencies involved in sharing the data processing load between the smartphone and an external computer, when the sensors on a smartphone are used to gather data on acceleration, rotation and orientation. The phone establishes a TCP connection to the computer for reliable delivery, which introduces a few milliseconds of initial handshaking delay, after which the data is transmitted with regular acknowledgments over the wireless channel. In one approach, a continuously running MATLAB script on the external computer reads these sensor values and executes the fall detection technique described above to determine if the subject with the smartphone has suddenly fallen down. If a fall is detected, peripheral sensors, such as the Microsoft KINECT®, device can be activated, which can capture visuals of the monitored patient. For comparison, the data analysis, that is, the fall detection technique, is performed on the smartphone. If a fall is detected, the smartphone sends a trigger to the computer using a TCP connection and activates the KINECT® device.

Figure 21:
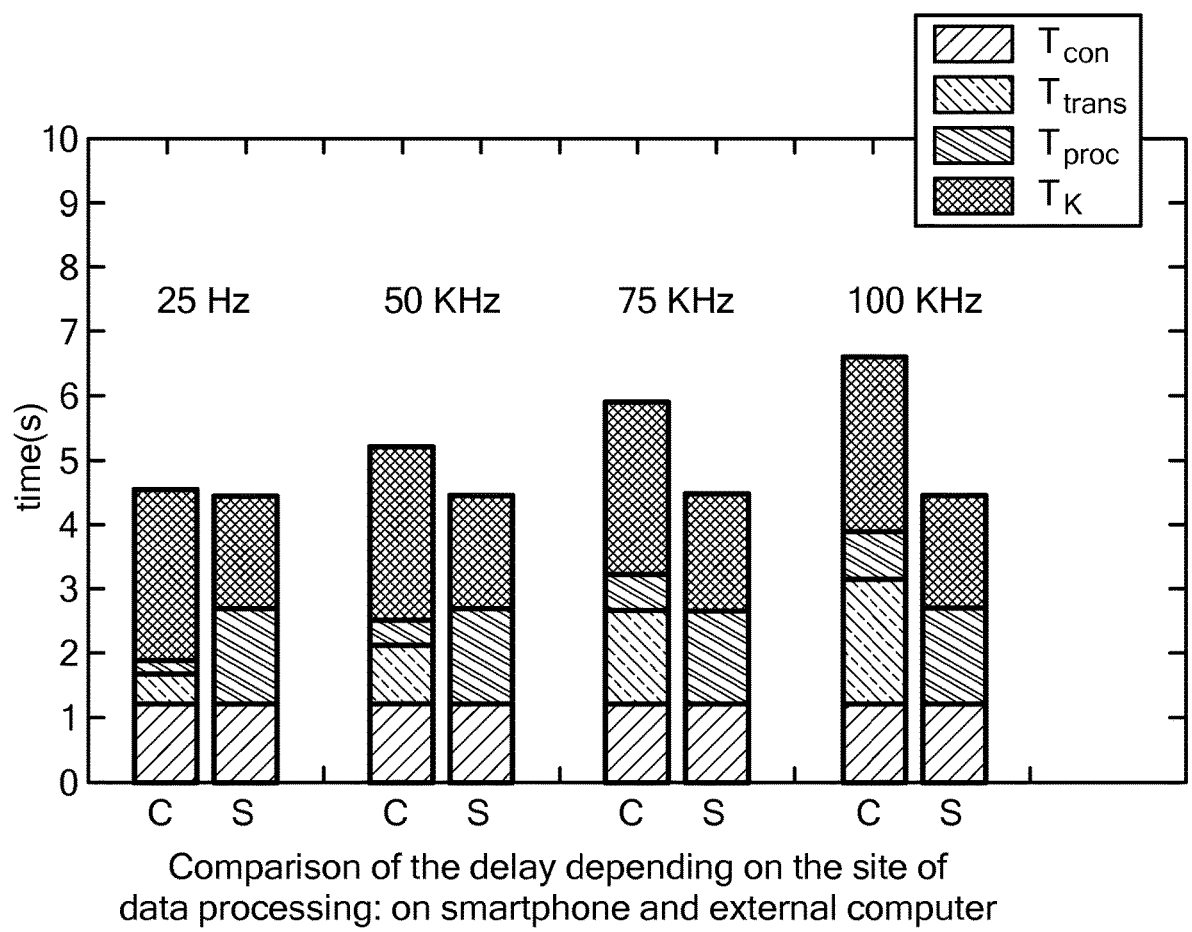
FIG. 21 is a graph comparing the time delay of the site of data processing on a smartphone to an external computer.

FIG. 21 compares the delay for these two approaches at different data sampling rates of 25 Hz, 50 Hz, 75 Hz, and 100 Hz. In FIG. 21, the computer-based approach is indicated by "C", and the smartphone-based approach is indicated by "S." The total delay is composed of the times it takes to (i) analyze the data ($T_{proc}$), (ii) connect to the TCP server running on the computer ($T_{conn}$), (iii) send the data ($T_{trans}$), and (iv) trigger the KINECT® device ($T_K$). As can be observed from the results, from the viewpoint of latency, it is much better to analyze the data on the smartphone and trigger the KINECT® device if a fall is detected.

Smartphones not only serve as personal communication devices and a convenient way to access to the Internet, but also as powerful processing platforms. The latest commercially available models provide computational capability in the range of 1.5 GHz dual-core processors and 1-2 GB of RAM, depending on the handset maker. The smartphone can act as a central gateway between the sensor assembly or assemblies and a computing cloud, capable of relaying data and inferences back and forth, as well as selecting the computational resource appropriate for the processing tasks. In one embodiment, for the end to end implementation, the Amazon Elastic Compute Cloud (Amazon EC2) can be used. The elastic nature of this service allows the system to instantly scale to meet spikes in traffic or demand. Parameters that are used in this decision framework are the energy cost of processing, the overhead of transmitting data over the wireless channel in terms of bandwidth use, and the processing latency to complete the task.

While higher sample rates generate less error during the prediction, lower sample rates are better in terms of battery consumption. That is, the phone uses less battery power when collecting data from the sensors every 40 ms (25 Hz), than when polling the sensors every 10 ms (100 Hz). Thus, the smartphone can continuously track and predict the sensor data from the sensor array(s), and when marked deviations are observed, increase the duty cycles of those particular sensors.

As one example of a processing function that occurs for real-time monitoring of neurological information, using only the sensor assembly data, the smartphone processor can perform electric field encephalography (EFEG) data preprocessing, artifact removal, raw and averaged data visualization, including causality, classification, and source reconstruction analyses.

As another example, using data from an entire neural network, including one or more sensor assemblies, smartphone sensors, and a motion capture device, such as the KINECT®, the smartphone can timestamp and synchronize the data from the multiple sensor streams, and undertake a first round of data aggregation and compression. It can also undertake cross-correlation among the sensor data to identify matches of neural activity spikes with the observed sensor data, such as changes in accelerometer or orientation readings.

In a further example, using, for example, the Amazon Elastic Compute Cloud, time series analysis and autocorrelation studies can be performed on massive volumes of historical data that are collected by the smartphone and stored in the cloud. One such study that requires large computational capability of the cloud processing is a time series decomposition where the temporal data for each of the sensors in the neural network for a given activity is broken down into long-term trends, sudden spikes, and cyclical components. This can help in identifying how neural activity changes with age, and its fluctuations over the short and long-term time scales.

Figure 20:
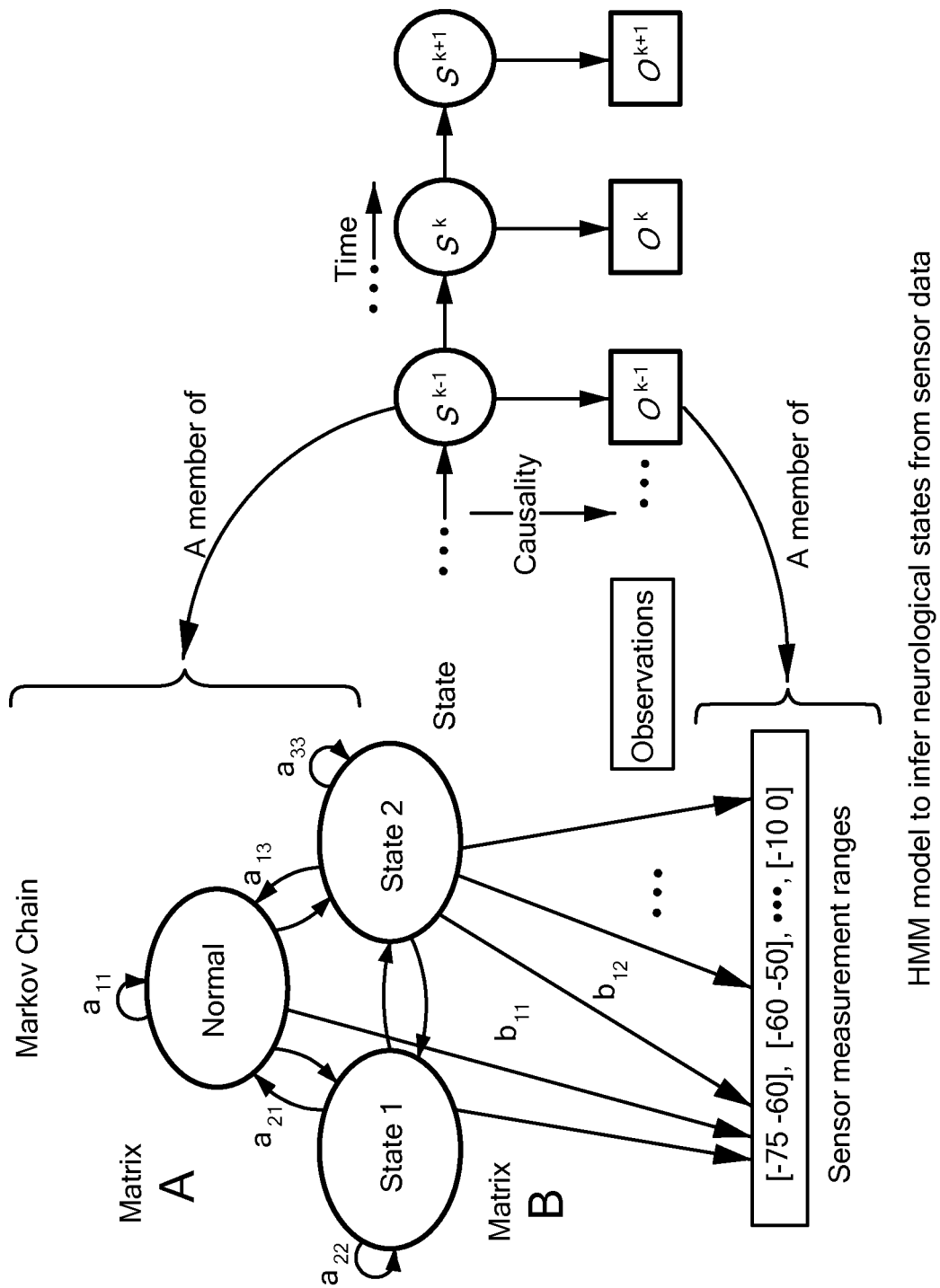
FIG. 20 is a schematic illustration of a Hidden Markov Model used to infer neurological states from sensor data.

The information from the sensor arrays, nearby detected sensors, such as the Microsoft KINECT®, and sensors within the smartphone can be provided as inputs to Hidden Markov Models (HMMs) to raise contextual awareness of the raw sensor data. A HMM includes a Markov chain whose states are hidden, as opposed to observable variables that are resultants of hidden states. In the neural network, the neurological states {normal, $S_1$, $S_2$} form a Markov chain as shown in FIG. 20. Considering a given sensor type, the range of the sensor measurements can be defined as the boundary values $\{[O^{min}_1, O^{max}_1], [O^{min}_2, O^{max}_2], \ldots, [O^{min}_N, O^{max}_N]\}$ for the N classes of observations. The HMM allows the probabilistic mapping of a given observation to each of the neurological states, one of which is responsible for causing these observations to occur.

Simple daily activities, such as watching TV, may introduce temporary changes in the stress level and the mental state of the patient depending on the program content, and it can be helpful to identify the context of sudden changes in the neural signal, if any, to distinguish more serious conditions, such as stroke. At the time of initialization, the smartphone can request an estimation of the living space of the patient with coordinates of key facilities and equipment, such as TV, washroom, exercise machine, dining table, among others, for example, through a drop-down menu. The assisted GPS capability (AGPS) of the smartphone helps in localization of the patient within a room in the facility of interest. Consider as an example a subject watching TV. The accelerometer can detect if the subject is undergoing continuous motion, suggesting a vigorous physical activity. If no continuous motion is detected, then the orientation of the phone (and hence, the subject) with respect to the Earth's magnetic axis is checked using the magnetometer. The point location of the AGPS as well as the orientation along the line of sight to the TV can indicate with high probability that the patient is watching TV. Thus, the HMM output in this scenario is weighted down as a non-risk stage, given that sudden changes in neurological states are likely due to the visual sensory inputs.

As noted above, in one embodiment, the sensor system employs Bluetooth technology as the underlying channel access method, which is a low-energy standard, suitable for wireless connectivity over short distances (typically <10 m). Bluetooth accommodates 7 active connections (slave devices) for a single master device, and additional devices can be placed in a low-power parked mode. The master, for example, the smartphone, is responsible for polling the slaves nodes, aggregating the data, and sending a compressed set of readings to the Internet cloud for comprehensive processing. It will be appreciates that alternative communication technologies, such as using radio, can be employed.

The sensor assembly can be configured to transmit signals in the medical body area network transmission band of 2360 to 2400 MHz recently specified by the Federal Communications Commission. Because this frequency band is heavily used, the system can employ a statistical activity model to identify the best frequency bands for transmission. These activity models are also used to formulate channel access schemes with interference avoidance with higher priority users, and ensure that data reporting requirements of the neurological signals are met with acceptable latency overhead.

The system can use a channel hopping pattern for avoiding portions of the frequency within the MBAN band that exhibit high levels of interference. Moreover, whenever there is a statistically high possibility of higher priority users within the MBAN band, a sensor array can pause an ongoing transmission, and lower the probability of selecting that subchannel in the next round of its hopping sequence. For other lower priority/peer-level users, however, the system can continue to include that particular subchannel in its hopping sequence, thereby allowing more numbers of distinct hopping sequences within the system's neural network. The core operational technique is first identifying a distribution function that gives the probability of spectrum being available at a given frequency f and for time duration t, which evolves with time, weighting recent measurements higher than those obtained earlier for the same external conditions. This distribution is used for selecting the set of channels for the hopping sequence.

The present system involves the dynamic leveraging of channel selection under different priority transmitters in the MBAN band. Extensive investigations have been carried out on the impact of coexisting users with different priorities within the wireless medical telemetry service (WMTS) band, which has been re-served by the FCC in the (i) current digital television (DTV) channel 37 between 608-614 MHz, (ii) lower-L band (1395-1400 MHz), and the (iii) upper-L band (1427-1432 MHz). Military and governmental agencies have a priority access in the lower-L band spectrum with a number of operational radars. In addition, the upper-L band and the lower-L bands are used by non-medical telemetry companies on a priority access and equal-access basis, respectively. As an example case, these studies have revealed that the lower-L band has intermittently transmitted signals displaced by 0.5 MHz from the center-frequency. Thus the channel is not available for continuous use by the medical telemetry sensors. Hence, there is a need to identify these higher priority signals and select portions of the spectrum that have higher likelihood of being available for longer durations of time. Various channel selection schemes based on pre-determined activity patterns can be used. See, for example, R. Doost-Mohammady and K. R. Chowdhury, "Enhancing Wireless Medical Telemetry through Dynamic Spectrum Access," Proc. of IEEE ICC, June 2012; R. Doost-Mohammady and K. R. Chowdhury, "Transforming Healthcare and Medical Telemetry through Cognitive Radio Networks", IEEE Wireless Communications Magazine, Vol. 19, No. 4, August 2012.

The system and process for measuring electromagnetic activity of the brain as described herein can provide a number of advantages. The EFEG measurement modality results in high resolution local measurements, while also providing for globally referenced EEG measurements. The sensor system provides significant improvement in the signal-to-noise ratio. The sensor assembly of the sensor system is unobtrusive, has a small footprint, is self-contained, can be operated wireless, and locally referenced.

The sensor assembly can be quickly placed on a subject's head and similarly it can be quickly removed. The sensor array works with a variety of hair types. The electrodes of the sensor assembly can be used dry or with an electrolyte gel. The sensor system can be used for continuous monitoring, for example, 24/7, of a subject's brain activity to provide low-profile, real-time monitoring of brain activity.

The sensor system can communicate with a variety of processors or other devices, such as a smartphone, laptop computer, or tablet computer. Communication can be via a wired connection or a wireless connection. The sensor system includes a measurement system including hardware and algorithms for data transfer, data preprocessing and analysis.

The present system is applicable in a variety of fields. The system can be used for functional brain imaging at high temporal and spatial resolution, for pattern recognition and cognition. The system can be used for conducting brain research, for example, to investigate neural correlates of vision and speech, aging, sleep, diseases such as epilepsy, Alzheimer's disease, Parkinson's disease, ALS, stroke, autism, depression, and traumatic brain injury. The system can be used for investigating human-machine and brain-computer interfaces.

The system can include one or several sensor assemblies worn by a subject to gather brain activity data along with other sensors, such as those found in a smartphone or other devices, such as an image and/or sound capture device. The system can be used as a neural network and can be used to provide context data for a subject. The system can be integrated into a medical body area network for the subject.

It will be appreciated that the various features of the embodiments described herein can be combined in a variety of ways. References to a smartphone herein include other devices that may be worn or carried by the subject.

The present invention has been described with reference to the preferred embodiments. It is to be understood that the invention is not limited to the exact details of construction, operation, exact materials or embodiments shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. A sensor assembly for measuring electromagnetic activity of a brain of a subject, comprising:
a support plate having first and second sides;
a plurality of electrodes mounted on and protruding from the first side of the support plate and supported for orientation toward and electrical contact with the subject's scalp, the plurality of electrodes arranged in a spaced array on the support plate, one of the plurality of electrodes comprising a reference electrode, each remaining electrode of the plurality of electrodes comprising an active electrode, the support plate configured to be attached to the subject with the plurality of electrodes oriented for electrical contact with the subject's scalp;
a plurality of amplifiers mounted on the second side of the support plate, each amplifier of the plurality of amplifiers in electrical communication with the reference electrode and in electrical communication with an associated one of the active electrodes to receive signals from the reference electrode and the associated ones of the active electrodes indicative of electric field activity of the brain and to amplify potential differences between each associated one of the active electrodes and the reference electrode; and
a microcontroller in communication with the plurality of amplifiers to receive signals from the plurality of amplifiers representative of the amplified potential differences between the reference electrode and the active electrodes, the microcontroller including a processor operative to determine, using the amplified potential difference signals, a tangential electric field component indicative of an electric field generated by electromagnetic activity of the brain;
wherein the microcontroller is further operative to determine a weighted average from a sum of potential signals from each active electrode relative to the reference electrode multiplied by a component of a distance to the reference electrode, the sum divided by a further sum of the square of the distance components.

2. The sensor assembly of claim 1, wherein the microcontroller is further operative to determine a weighted average from a sum of potential signals from each electrode divided by a number of the plurality of electrodes.

3. The sensor assembly of claim 1, wherein the microcontroller is further operative to determine a weighted average from a sum of potential differences from each electrode relative to the reference electrode multiplied by a component of a distance to a center of the arrangement of the plurality of electrodes, the sum divided by a sum of the distance to the center of the arrangement to the fourth power.

4. The sensor assembly of claim 1, wherein the microcontroller is further operative to determine a higher order derivative of an electric potential.

5. The sensor assembly of claim 1, further comprising a transceiver for sending and receiving signals between the microcontroller and an external device.

6. The sensor assembly of claim 1, further comprising a wireless data transmission port.

7. The sensor assembly of claim 1, wherein each of the plurality of electrodes comprises a conductive pin.

8. The sensor assembly of claim 1, further comprising a housing attached to the support plate, the plurality of amplifiers and the microcontroller disposed within the housing.

9. The sensor assembly of claim 1, further comprising a further sensor assembly, the sensor assembly and the further sensor assembly formed with a headband to mount to a head of the subject.

10. The sensor assembly of claim 1, wherein each amplifier is in electrical communication with an associated analog to digital converter, each analog to digital converter in electrical communication with the processor of the microcontroller.

11. The sensor assembly of claim 1, wherein the subject comprises an animal, a mammal, or a human.

* * * * *